(12) United States Patent
Fu

(10) Patent No.: US 7,440,817 B2
(45) Date of Patent: Oct. 21, 2008

(54) METHOD AND CONTROL UNIT FOR MEDICATION ADMINISTERING DEVICES

(76) Inventor: Liang Fu, 12046 Gatewater Dr., Potomac, MD (US) 20854

( * ) Notice: Subject to any disclaimer, the term of this patent is extended or adjusted under 35 U.S.C. 154(b) by 268 days.

(21) Appl. No.: 11/163,500

(22) Filed: Oct. 20, 2005

(65) Prior Publication Data

US 2007/0093935 A1   Apr. 26, 2007

(51) Int. Cl.
G06F 17/00 (2006.01)
(52) U.S. Cl. ............... 700/237; 700/244; 700/236; 221/15
(58) Field of Classification Search .............. 700/237, 700/236, 244; 211/15
See application file for complete search history.

(56) References Cited

U.S. PATENT DOCUMENTS

| | | | |
|---|---|---|---|
| 4,573,606 A | 3/1986 | Lewis et al. | |
| 4,638,923 A | 1/1987 | Mines, Jr. et al. | |
| 4,682,299 A | 7/1987 | McIntosh et al. | |
| 4,695,954 A * | 9/1987 | Rose et al. | 700/236 |
| 4,785,932 A | 11/1988 | Checke | |
| 4,785,969 A * | 11/1988 | McLaughlin | 700/237 |
| 4,797,283 A | 1/1989 | Allen et al. | |
| 4,831,562 A | 5/1989 | McIntosh et al. | |
| 4,837,719 A | 6/1989 | McIntosh et al. | |
| 4,942,544 A | 7/1990 | McIntosh et al. | |
| 4,953,745 A | 9/1990 | Rowlett, Jr. | |
| 4,962,491 A * | 10/1990 | Schaeffer | 221/15 |
| 4,970,669 A | 11/1990 | McIntosh et al. | |
| 5,088,056 A | 2/1992 | McIntosh et al. | |
| 5,159,581 A | 10/1992 | Agans | |
| 5,181,189 A | 1/1993 | Hafner | |
| 5,200,891 A * | 4/1993 | Kehr et al. | 221/15 |
| 5,221,024 A | 6/1993 | Campbell | |
| 5,408,443 A * | 4/1995 | Weinberger | 221/3 |
| 5,522,525 A | 6/1996 | McLaughlin et al. | |
| 5,710,551 A * | 1/1998 | Ridgeway | 700/231 |
| 5,826,217 A | 10/1998 | Lemer | |
| 5,838,224 A | 11/1998 | Andrews | |
| 5,852,590 A | 12/1998 | de la Huerga | |
| 5,883,370 A | 3/1999 | Walker et al. | |
| 5,990,782 A | 11/1999 | Lee | |
| 6,032,085 A | 2/2000 | Laurent et al. | |
| 6,119,892 A | 9/2000 | Laurent et al. | |
| 6,131,765 A | 10/2000 | Barry et al. | |
| 6,259,654 B1 | 7/2001 | de la Huerga | |
| 6,263,259 B1 * | 7/2001 | Bartur | 700/240 |
| 6,281,798 B1 | 8/2001 | Laurent et al. | |
| 6,294,999 B1 * | 9/2001 | Yarin et al. | 705/2 |
| 6,335,907 B1 | 1/2002 | Momich et al. | |

(Continued)

*Primary Examiner*—Gene O. Crawford
*Assistant Examiner*—Timothy R Waggoner

(57) ABSTRACT

A method and control unit for medication administering devices. The first aspect of the present invention is automatic programming of the scheduled events. The second aspect is simple user-request expression. The third aspect is guided user operation. The forth aspect is automatic medication-storage mapping. The fifth aspect is no clock setting. Prior art systems typically require the user to figure out a loading-scheduling plan, follow the plan to load the medications, program the scheduled events and tell the system how the medications are stored (manual medication-storage mapping). The system of the present invention does the opposite: it figures out the loading-scheduling plan, guides the user to load the medications, program the scheduled events, and establishes medication-storage mapping, all automatically. The system of the present invention is extremely easy to use, and vision-impaired users can easily use it.

7 Claims, 11 Drawing Sheets

U.S. PATENT DOCUMENTS

| | | |
|---|---|---|
| 6,338,535 B1 | 1/2002 | Rickert |
| 6,380,858 B1 | 4/2002 | Yarin et al. |
| 6,401,991 B1 * | 6/2002 | Eannone ................ 221/15 |
| 6,529,446 B1 | 3/2003 | de la Huerga |
| 6,554,136 B2 | 4/2003 | Priebe |
| 6,594,549 B2 * | 7/2003 | Siegel ................ 700/237 |
| 6,607,094 B2 | 8/2003 | MacDonald |
| 6,611,733 B1 | 8/2003 | de la Huerga |
| 6,626,358 B1 * | 9/2003 | Breimesser et al. ......... 235/380 |
| 6,834,775 B1 | 12/2004 | Collins |
| 6,845,064 B2 | 1/2005 | Hildebrandt |
| 6,848,593 B2 | 2/2005 | Papp |
| 6,871,783 B2 | 3/2005 | Kaafarani et al. |
| 2001/0002025 A1 | 5/2001 | Rolf-Dieter et al. |
| 2001/0022758 A1 | 9/2001 | Howard |
| 2001/0028308 A1 | 10/2001 | de la Huerga |
| 2002/0000917 A1 | 1/2002 | Rubenstein |
| 2002/0027507 A1 | 3/2002 | Yarin et al. |
| 2002/0067270 A1 | 6/2002 | Yarin et al. |
| 2002/0070227 A1 | 6/2002 | Ferruccio |
| 2002/0113077 A1 | 8/2002 | Topliffe et al. |
| 2002/0118604 A1 | 8/2002 | Sharma et al. |
| 2002/0130138 A1 | 9/2002 | Crozet et al. |
| 2002/0147526 A1 | 10/2002 | Siegel |
| 2003/0042167 A1 | 3/2003 | Baiz et al. |
| 2003/0099158 A1 | 5/2003 | de la Huerga |
| 2003/0127463 A1 | 7/2003 | Varis |
| 2003/0146848 A1 | 8/2003 | Kohlin |
| 2003/0222090 A1 | 12/2003 | Abdulhay et al. |
| 2004/0039481 A1 | 2/2004 | de la Huerga |
| 2004/0133305 A1 | 7/2004 | Jean-Pierre |
| 2004/0158350 A1 | 8/2004 | Ostergaard et al. |
| 2004/0172163 A1 | 9/2004 | Varis |
| 2004/0182873 A1 | 9/2004 | Baum |
| 2004/0210488 A1 | 10/2004 | Doherty |
| 2004/0256406 A1 | 12/2004 | Allen |
| 2005/0041531 A1 | 2/2005 | Sekura |
| 2005/0109658 A1 | 5/2005 | BindFord |
| 2005/0150805 A1 | 7/2005 | Burchell |

* cited by examiner

METHOD AND CONTROL UNIT FOR MEDICATION ADMINISTERING DEVICES

BACKGROUND OF THE INVENTION

1. Field of Invention

This invention relates to managing and administering medications, especially to automated system for managing and administering medications.

2. Description of Prior Art

Presently, a doctor prescribes medication for a patient by writing on a standard prescription form, calling a prescription-filling facility, or entering into a specialized computer system (such as Computerized Physician Order Entry, or CPOE) with the prescription information, which normally includes the doctor's information, the patient's information, the medication identifier (name), and the usage information. The usage information usually includes schedule (e.g., one unit dose every morning, one unit dose every four hours, etc.), unit dosage (e.g., three tablets, 10 ml, etc.), and total daily dosage (e.g., 9 tablets, 40 ml., three unit doses, etc.).

For an inpatient, the prescription is usually filled by an in-hospital medication administration unit, and a nurse administers each unit-dose medication to the patient following the usage information.

For an outpatient, the prescription is usually filled by a pharmacy, and a pharmacist enters the prescription information into the pharmacy's computer system. The pharmacy's computer system prints a medication label with human-readable medication information (including medication identifier and the usage information, to be affixed on the container or bag). The patient has to follow the usage information to take the medication.

Taking a wrong medication, with a wrong dosage, or at a wrong time could result in ineffective treatment, complication, or even death. Many methods, systems, and devices have been developed or proposed in prior art to help nurses and patients adhere to usage information.

The healthcare facilities (hospitals, nursing homes, etc.) have adopted regulations and procedures in administering medication. According to the prior art, there are medication-administering systems for healthcare facilities, where the computer matches patient identification with prescribed medication before administering a unit-dose medication. The FDA has ruled (effective in 2006) that healthcare facilities must use barcode for patient identification matching.

For home-consumed medications, the responsibility for following usage information falls completely on the patient or the family members. In addition to prescription medications (Rx), a person may also take over-the-counter (OTC) medications and dietary supplements, which also have their own usage information. That further complicates the matter.

For simplicity and definiteness, unless otherwise specified, the term "medication" will in general include Rx, OTC, dietary supplements, with all application types (intake, topical, injection, inhaler, etc.) in all forms (liquid, gaseous, ornament, powder, pill, capsule, etc.). The term "user" will be used to refer to a person who takes medication. The term "scheduled event" will generally refer to an event that is scheduled to take place at a specified moment, but mostly it will refer to a unit dose of certain medication at a scheduled time.

According to the prior art, a user can choose one or several devices described in the following to assist him/her adhere to usage information at home.

A user can use a bulk medication organizer. A bulk medication organizer has multiple storage compartments, each for a type of medication. Examples of prior art designs include: U.S. patent application Pub. No. 2002/0130138 and 2001/0002025, U.S. Pat. Nos. 4,785,932 and 4,638,923. Bulk medication organizers represent the design of the lowest automation among all prior art designs. It is just slightly more organized than leaving medications in their original containers. Besides specific shortcomings of each individual design, bulk medication organizers suffer from the following common disadvantages:

(A1) They provide very limited help.
(A2) User has to label each storage compartment with usage information.
(A3) User has to keep time and track scheduled events with other means.

A user can use a dose-compartment medication organizer. A dose-compartment medication organizer has multiple dose compartments, each holding one or several medications to be taken at same time. Examples of prior art designs include: U.S. patent application Pub. No. 2005/0109658 and 2004/0256406, U.S. Pat. Nos. 6,554,136, 6,338,535, and 5,838,224. Besides the specific shortcomings of each individual design, dose-compartment medication organizers suffer from the following common disadvantages:

(B1) User has to figure out a loading-scheduling plan according to the usage information.
(B2) User has to follow the loading-scheduling plan to load the medications into the dose compartments.
(B3) Loading becomes dramatically complicated and tricky as the number of medications increases.
(B4) Practically they are not suitable for medications that require precise timing, or have very different or complex schedules.
(B5) It is very difficult to add a new medication since user has to find an existing group with compatible schedule and identify the corresponding dose compartments.
(B6) It is difficult to delete (cancel) a medication since the user has to search all dose compartments for that medication.
(B7) User has to label each dose compartment with schedule except for very simple and regular schedules (e.g., every morning).
(B8) User has to keep time and track the scheduled events with other means.

A user can use a medication reminder. A medication reminder produces visual, audible, or tactile alarm for scheduled events to remind the user. Examples of prior art designs include: U.S. patent application Pub. No. 2005/0150805, 2005/0041531, and 2003/0146848, and U.S. Pat. No. 6,845,064. The medication reminder may be equipped with a display or speaker to indicate the medication and unit dosage to be taken. A medication reminder may be used for a single medication, a group of medications with same schedule, or several medications with different schedules. Besides the specific shortcomings of each individual design, medication reminders suffer from the following common disadvantages:

(C1) User has to set the clock.
(C2) User has to program the medication reminder for each scheduled event.

Many prior art designs combine medication reminder with bulk medication organizer or dose-compartment medication organizer. Examples of prior art designs include: U.S. patent application Pub. No. 2004/0182873 and 2001/0022758, and U.S. Pat. Nos. 6,131,765, 5,990,782, and 5,826,217. Such designs overcome some of the disadvantages of the bulk (A2 and A3) and dose-compartment medication organizers (B7 and B8), but they incorporate the disadvantages of the medication reminder (C1 and C2).

A user can use a dose-compartment medication dispenser. A dose-compartment medication dispenser is similar to the above described dose-compartment medication organizer, except using motors to align (rotate) the dose-compartment with the outlet. Examples of prior art designs include: U.S. patent application Pub. No. 2003/0127463 and 2002/0118604, and U.S. Pat. Nos. 6,834,775, 5,159,581, and 4,573,606. Dose-compartment medication dispensers incorporate the disadvantages (B1) to (B6) of dose-compartment medication organizers and the disadvantages (C1) and (C2) of medication reminders. They have further common disadvantages:

(D1) Since now the order of dose compartments is tied to the sequence of dispensing, loading the medication and programming the scheduled events become even more complicated.

(D2) Most of them can only handle simple schedules (e.g., three times everyday).

(D3) Even if some of them can handle complex schedules, programming such schedules and loading the medications accordingly are very complicated and tricky, hence, practically prohibitive.

A user can use a bulk medication dispenser. Examples of prior art designs include U.S. patent application Pub. No. 2003/0222090 and 2002/0070227, U.S. Pat. Nos. 6,607,094 and 4,953,745. Bulk medication dispensers store each type medication in a storage compartment, similar to bulk medication organizers, but they can dispense the unit-dose medications according to scheduled events. Although bulk medication dispensers offer several advantages over other groups, e.g., efficient storage, easier loading and deleting, they suffer from the following common disadvantages:

(E1) User has to set the clock.

(E2) They typically require substantial user programming (E3) They require complex user-programming interfaces (some prior art designs require a PC to program a bulk medication dispenser).

(E4) User has to find appropriate storage compartment (original one for a refill or empty one for new) to load the medication.

(E5) User has to tell the system (through additional user programming) which medication is stored in which compartment.

As explained above, all these prior art designs require manual effort, or programming effort, or both. Generally speaking, the designs with low level of automation require low level of programming effort but high level of manual effort, the designs with high level of automation require low level of manual effort but high level of programming. This is a dilemma for the prior art designs. Both manual task and programming not only make prior art devices difficult to use, but also can cause errors.

These prior art designs have overlooked a crucial fact, namely, the majority of medication users by far are elderly people, who are least willing and able to perform such manual and programming tasks. Even if a device has some wonderful features, complicated manual operation or user programming could cause the users not to utilize these features, not to utilize them to their fullest capacity, or possibly to abandon it all together.

Furthermore, the designs that require user programming, especially those require substantial or complex user programming, are not suitable for some users, especially vision-impaired users. Some devices and designs are claimed to be suitable for vision-impaired users since audible alarms and voice messages are used instead of visual displays. As long as these devices and designs require user programming and clock setting, they pose a severe and often prohibitive challenge to vision-impaired users.

Methods have been developed or proposed in prior art to ease user operations, but most of them merely shift the user operation burden to professionals.

A user can have his/her medications prepackaged and use a prepackaged medication dispenser. A prepackaged medication dispenser dispenses unit-dose packages, each unit-dose package containing one or several medications to be taken at same time. This is similar to a dose-compartment medication dispenser, except that the unit doses are prepackaged by medication provider, instead of being loaded by the user. Examples of prior art designs include: U.S. patent application Pub. No. 2004/0158350 and 2003/0042167, U.S. Pat. Nos. 6,848,593, 5,221,024, and 4,797,283. Although it relieves user from grouping and loading the medications, this method imposes most restrictions upon the users among all prior art methods. Besides specific shortcomings of each individual design, this method suffers from the following common disadvantages:

(F1) All medications of a user have to come from a single provider that prepackages them, or they are left out.

(F2) Only the medications of same schedule can be prepackaged (together).

(F3) Practically, it is only suitable for long-term medications and medications with regular and simple schedules (otherwise, packaging instructions and programming are likely to be too complicated).

(F4) Each specific design of dispenser can only work with one type of package/magazine and vise versa.

(F5) Each specific design of packages requires a specific packaging line.

(F6) A user of a particular prepackaged dispenser is usually stuck with a specific provider (because of F4 and F5).

(F7) Each type of package/magazine can only handle certain types of medications.

(F8) Each type of package/magazine is only suitable to a certain amount of medications.

(F9) Only certain types of medications are suitable for pre-packaging.

(F10) It is impossible to add a new medication (user has to discard medications already packaged and reorder).

(F11) It is impossible to change the sequence of the medications (user has to discard medications already packaged and reorder).

(F12) It is very difficult to delete a medication unless user can identify it by appearance and discard them from every unit-dose package.

(F13) Cost is high due to service fees and wasted medications.

Generally speaking, any change in user's medication usually means discarding all prepackaged medications and reorder, since any confusion or error may have devastating consequences.

U.S. patent application Pub. No. 2004/0133305 and 2002/0000917, and U.S. Pat. No. 5,408,443 suggested that medication providers, e.g., pharmacies, provide a pre-programmed device (medication reminder plus storage, or medication dispenser) with filled medication. Besides specific disadvantages of each individual design, this method suffers from the following common disadvantages:

(G1) It is subject to cross contamination and hygiene problems since the devices will be passed to different users.

(G2) User has to bring the device from and to the medication provider for new medication, returning (when medication finishes), and having it reprogrammed (if doctor has directed any change).

(G3) It drastically changes the routines and increases the workload of the medication provider.
(G4) It generates additional service cost.
(G5) It can only be used for prescription medications (no help for non-prescription medications).

Also, remote administration of medication has been proposed. Examples of prior art designs include: U.S. patent application Pub. No. 2004/0210488, 2004/0172163, 2002/0147526, and 2002/0113077.

The basic idea of remote administration of medication is to let a caregiver (physician, nurse, or other qualified individual) to program the scheduled events for a user via Internet on a dedicated server. The dedicated server in turn controls a medication dispenser at user's residence (remote-controlled dispenser, usually a prepackaged dispenser) via a dedicated telephone line or other communication means (cable or wireless). Some prior art designs further require a local PC to control the dispenser. Basically, the caregiver takes over the manual and programming burden from the user. Besides specific shortcomings of each individual design, remotely controlled medication systems have the following common disadvantages:
(H1) They require large supporting system including infrastructure and personnel, which in turn require considerable initiative and investment.
(H2) The supporting systems must keep all medical record of a user, track and administrate all medications of the user.
(H3) They require collaboration and coordination of many parties, including the insurance company and other caregivers of the user.
(H4) Once enrolled, a user is likely to be stuck with a system for a long time since it is difficult to switch to another system.
(H5) The Internet can hardly be secured completely, and computer systems, especially large ones, can hardly avoid malfunction; hence, the user is exposed to additional risks, such as stolen personal and medical information, administration of a wrong medication, a wrong dose, or a wrong time.
(H6) The caregiver has to come to the user's home to load the dispenser periodically or anytime there is a change in user's medication.
(H7) A high maintenance cost is charged to the user.

It has been proposed in prior art to use memory devices to store machine-readable information. Examples of prior art designs include: U.S. patent application Pub. No. 2004/0039481, 2003/0099158, 2002/0067270, 2002/0027507, and 2001/0028308, U.S. Pat. Nos. 6,611,733, 6,529,446, 6,380,858, 6,335,907, 6,294,999, 6,259,654, 5,852,590, 5,522,525, and 5,181,189 proposed similar ideas where memory strip, IC chip, or barcode that contains schedule and unit-dosage information were attached to (or made on) the package of each medication. When the package is correctly mounted on the medication device, the memory strip, IC chip, or barcode are connected or aligned with a reader, so the stored information can be read and used to set the scheduled events. These designs have the following common disadvantages:
(I1) They require specially designed medication containers.
(I2) The memory strip, IC chip and barcode have to be affixed on the packages with accurate position and orientation.
(I3) They require the specially designed medication containers be accurately mounted on the device such that the memory strip, IC chip, or barcode (hence the medication) are aligned with the reader or a set of electrical leads connect with that of the device.

In addition, U.S. Pat. Nos. 6,335,907 and 5,181,189 in this group require
(I4) each medication to use a device.

U.S. patent application Pub. No. 2004/0039481, 2003/0099158, 2002/0067270, 2002/0027507, and 2001/0028308, U.S. Pat. Nos. 6,611,733, 6,529,446, 6,380,858, 6,294,999, 6,259,654, 5,852,590, and 5,522,525 in this group require
(I5) redundant components (memory readers and control units), each for a medication.

When used with a remote sensing method, such as RF tags as suggested in these prior art designs, multiple readers are
(I6) subject to interference.

U.S. Pat. Nos. 6,281,798, 6,119,892, 6,032,085, and 4,695,954 proposed designs with detachable card (smart card or magnetic card) that stored the machine-readable information. The detachable card is inserted into the proposed user devices that can read the information and set the scheduled events. Although these designs can handle multiple medications, without providing a convenient method for user to load the medications into the devices, they require:
(I7) the device or a detachable storage to be filled by a pharmacy, or
(I8) additional user operation, additional components, and additional controls.

In general, all these prior art designs with memory devices
(I9) have limited applications,
(I10) restrictive configurations, and
(I11) very little flexibility.

Furthermore, all these designs with memory devices
(I12) require users to set clock.

Finally, all of the prior art programmable devices and systems have three common disadvantages:
(J1) The methods of user-request expression (loading, refilling, modifying, deleting, taking emergency dose, etc) are too complicated and complicated user-input interfaces are required.
(J2) They do not provide guided user operations.
(J3) They do not provide automatic medication-storage mapping.

In order to achieve certain level of automation, such as automatic dispensing, a mechanism is needed for the system to tie the medication with its storage. For definiteness, this mechanism will be called medication-storage mapping. When a user loads a medication to a prior art system, the user not only has to program the scheduled events but also has to tell the system where the medication is stored through additional user programming, so that the system can establish the medication-storage mapping. This kind manual medication-storage mapping not only is cumbersome but also can cause errors, prompting some prior art designs to require pharmacy to load the medications, or to use redundant components or devices, each handling one medication.

In conclusion, despite the improvements of the method and system for managing and administering medications, many problems remain unsolved, or their solutions remain unsatisfactory. There is definitely a need for a method and system that substantially overcome the aforementioned disadvantages of the prior-art designs and provide overall satisfactory results.

BRIEF SUMMARY OF THE INVENTION

The present invention is a method and control unit for medication administering devices. The first aspect of the present invention is automatic programming of the scheduled events for medications. Hence the user programming, the user-programming interface, and user programming errors are all eliminated. The second aspect is simple user-request expression. Hence both user input and user-input interface are extremely simple. The third aspect is guided user operation.

The system guides the user to complete necessary operations corresponding to the user requests. Hence user operations are significantly simplified. The forth aspect is automatic medication-storage mapping. While with easy loading, the system establishes medication-storage mapping automatically without any additional user effort. The fifth aspect is no clock setting. Hence clock-setting interface is eliminated and the user-input interface is further reduced. Prior art systems typically require the user to figure out a loading-scheduling plan, follow the plan to load the medications, program the scheduled events, and tell the system how the medications are stored (manual medication-storage mapping). The system of the present invention does the opposite: it figures out the loading-scheduling plan, guides the user to load the medications, programs the scheduled events, and establishes medication-storage mapping, all automatically. Each of the five aspects of the present invention overcomes a number of the aforementioned prior art disadvantage. Each of them reduces or simplifies the physical complexity, the components, and the user operations. Each of them reduces potential errors associated with the prior art designs. Combining these aspects together, the present invention overcomes all aforementioned disadvantages of the prior art designs, significantly simplifies or reduces the complexity, the components, the potential operation errors of the prior art designs, and greatly simplifies the user operations. The method and control unit of the present invention can be adopted to control all types of medication administering devices (existing and future developed), is very flexible (basically no restriction in configuration, dimension, or interconnection of the components), and easy to use. Due to its high level of automation and ease of use, vision-impaired users and other users that are excluded by prior art systems can easily use the system of the present invention.

The major objectives and advantages of the present invention are:

(1) To provide a method and control unit that satisfies practically all needs for medication management and administration.

(2) To provide a method and control unit that automatically programs the scheduled events for each medication, hence eliminates user programming, user-programming interface, and user-programming error.

(3) To provide a method and control unit that automatically tracks the scheduled events and takes appropriate actions.

(4) To provide a method and control unit that has a minimal user-input interface and allows users to express requests with very simple manners.

(5) To provide a method and control unit that guides the user to complete all necessary user operations.

(6) To provide a method and control unit that automatically establishes medication-storage mapping without any additional user effort.

(7) To provide a method and control unit that does not require clock setting and clock-setting interface.

(8) To provide a method and control unit that has a minimal user-input interface, requires minimum and simple user operations, and reduces the user-operation errors associated with prior art designs.

(9) To provide a method and control unit that can be used by any number of users, can control any number of devices, can handle any number of medications, with any precise timings, any different schedules, and any complex schedules.

(10) To provide a method and control unit that vision-impaired users and other users that are excluded by prior art systems and devices can easily use.

(11) To provide a method and control unit that is so easy to use hence there is no longer a need for professional assistance or having medications prepackaged.

(12) To provide a method and control unit that user are not required to subscribe to any organization for managing their medications and no large supporting system is needed.

(13) To provide a method and control unit that does not require redundant components.

(14) To provide a method and control unit that can be adopted for all types of medication administering devices.

(15) To provide a method and control unit that basically has no restrictions on configuration, dimension, interconnection among its components, and detailed design of the controlled device, giving the device manufacturers maximum freedom in designing their devices.

(16) To provide a method and control unit that does not require medication providers to drastically change their routines, equipments, or medication packages.

(17) To provide a method and control unit that allows users to freely choose their medication providers and medication administering devices.

(18) To provide a method and control unit that is of low cost to users.

(19) To provide a method and control unit that overcomes all aforementioned disadvantages of the prior art designs.

BRIEF DESCRIPTION OF THE SEVERAL VIEWS OF THE DRAWING

In the drawings, closely related figures have the same number but different alphabetic suffixes.

DETAILED DESCRIPTION OF THE INVENTION

To best explain the fundamental idea of the present invention, the most basic form of the present invention will be described. It should not be construed in any way as limitation or restriction of the present invention.

PREFERRED EMBODIMENT

Figure 1:
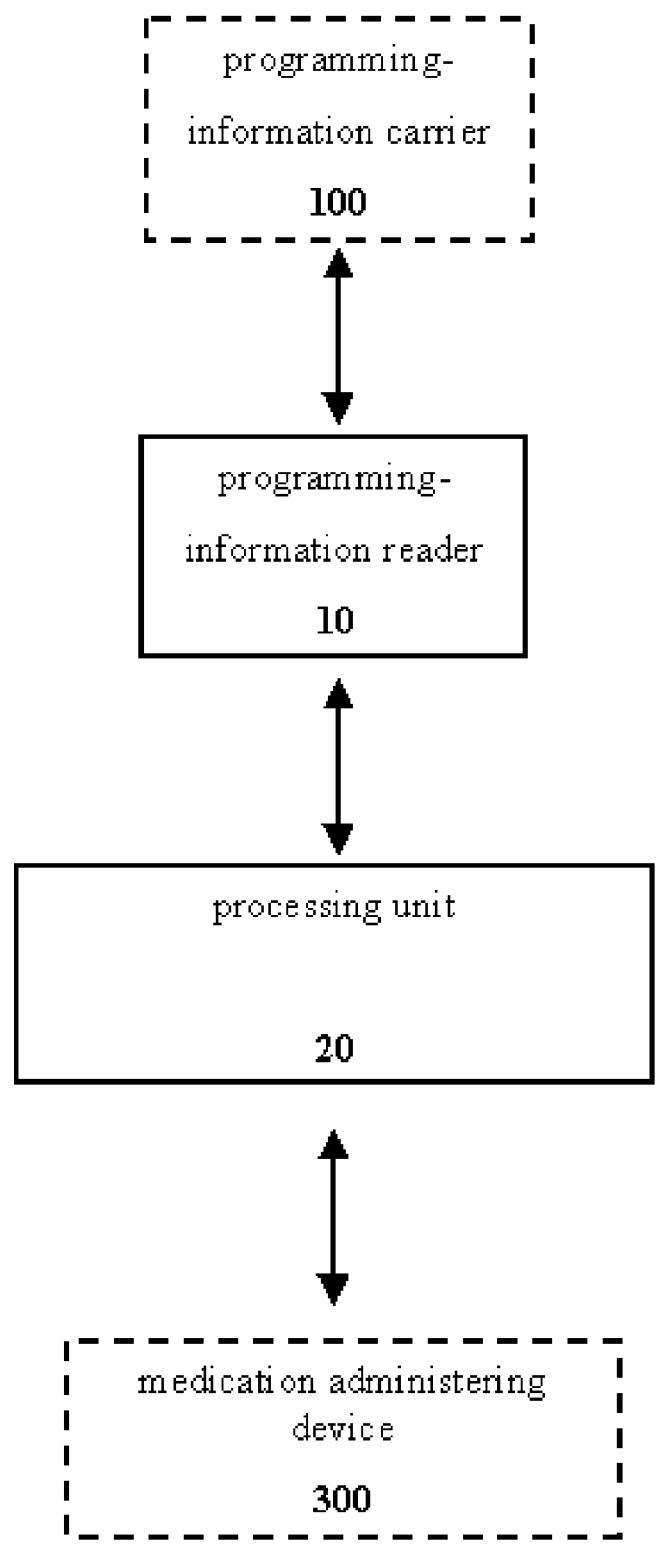
FIG. 1 is the block diagram of the major components of the control unit of the present invention.

Refer to FIG. 1 for the major components of the control unit of the present invention. The control unit comprises two major components, a programming-information reader 10 and a processing unit 20. The programming-information reader 10 is capable of reading programming information encoded in machine-readable format according to an encoding protocol. The programming information is stored in a programming-information carrier 100. The present invention uses various types of programming information in various suitable situations. Typical ones include medication identifier, usage information, user identifier, and user requests, which can be selectively combined and stored in a single programming-information carrier or stored separately. For clarity and simplicity, the preferred embodiment section mainly concerns two types of programming information unless otherwise stated. The first one contains both medication identifier and usage information of a medication, and the second one contains only the medication identifier (to be used with preloaded usage information, as explained later). Other examples of programming information will be discussed in later sections. The control unit can be adopted to control any type of medication administering device 300, and all typical examples of such devices will be given later. The medication administering device 300 will also be referred as the controlled device. The control unit plus the controlled device will be referred as the medication administering system, or simply the system.

The programming-information is considered as an external component, just like human-readable usage information to prior art systems. The dashed boxes in FIG. 1 indicate that both programming-information carrier 100 and the controlled device 300 are external components (to the control unit). Medication provider (pharmacy, mail-order filler, drug or dietary-supplement manufacturer, etc.) or prescription generator (doctor) may provide the programming information. Standard templates or preloaded usage information may also be used. All these types will be explained in detail.

The two major components of the control unit described above are logical divisions rather than physical divisions of the control unit of the present invention. Physically, these two major components can be separate components or integrated together. They can also be broken down to further granular components. The sub-components of the two major components may also be shared or selectively moved from one major component to another. These two major components (or some of their sub-components) may even be integrated with the external components, namely, the programming-information carrier 100 or the controlled device 300 (examples will be given later).

The arrows in FIG. 1 represent communication links among all components (internal and external). Any suitable communication means, wired or wireless, currently existing or developed in the future, can be used. There are basically no restrictions on configuration, dimension, interconnection, or detailed designs for each component. With such flexibility, the makers of the system virtually can choose any type of medication administering device, with any configuration, dimension, interconnection, and detailed designs they like. They can even make modules that contain part of the system to work with complementary modules made by others. The flexibility is a major advantage of the present invention over the prior art designs.

In the following, the term "scan" means to use the programming-information reader to read the programming information, unless otherwise stated.

The first aspect of the present invention is automatic programming of the scheduled events. Programming information that contains usage information allows programming of the scheduled events for a medication. Of course, the programming information may contain directly the scheduled events. A scheduled event can be either one-time or recurring. A one-time scheduled event has a specified date and time and automatically expires when the specified date and time passes. Recurring scheduled event occurs repeatedly according to a predetermined pattern (e.g., three times a day), and it can be viewed as multiple one-time scheduled events. The programming information may also be encrypted for information security. It may further contain information to indicate the type of the encoding protocol and the format if more than one encoding protocol or format are used. It may also contain a "signature" (e.g., a mark or a special format) to distinct it from other information.

Instead of using a conventional user-programming interface (which consists of buttons, keypad, touch screen) to program the scheduled events as with typical prior art designs, the user of the system of the present invention simply scans the programming information. The programming-information reader 10 converts the encoded programming information into appropriate programming-information signals, and transmits them to the processing unit 20. The programming-information reader 10 can be active (i.e., actively scans programming information), passive (i.e., passively receives programming information transmitted by the programming-information carrier), or both (e.g., prompts the carrier to transmit and then passively receives). The processing unit 20 decodes the programming information from the programming-information signals according to the encoding protocol, and programs the scheduled events automatically using the programming information. The user programming, the user-programming interface, and the user programming errors are all eliminated. The processing unit 20 stores the scheduled events and generates control signals for each scheduled events. The control signals are sent to the controlled device, which takes appropriate actions in response to the control signals.

The major difference between this aspect of the present invention and the prior art designs with memory devices is that the present invention has basically no restriction on configuration, dimension, or interconnection of the components basically no restrict in configuration, no redundant components are required, no restriction on the number of the controlled devices or the medications, no restriction on medication containers and their relations to the system, and no restrictions on the type of the memory media, the positions and orientations of the programming information carrier.

It should be emphasized that the machine-readable programming information of the present invention differs fundamentally from the "electronic prescription" proposed in prior art, although the physical carrier and reader, or even the stored information itself, may be the same or similar in both cases. The distinction is how and for what purpose the information is used. The programming information of the present invention is used to automatically program the scheduled events and express user requests (explained later), while the electronic prescription of the prior art does not have the same function and is not used for the same purpose.

The proposed use of electronic prescription in prior art is for pharmacies, medication order filling facilities, and medication packagers, to fill a prescription order. For example, the U.S. Pat. No. 6,871,783 proposed a prescription module that carries doctor's prescription electronically. U.S. Pat. No. 5,883,370 proposed to store prescription in barcode for use with "pharmacy vending machines". Such systems use the "order information", namely, the name and total amount of a medication. Although the usage information is included in the electronic prescription, it is simply passed to the user in human-readable form, e.g., shown on a display or printed on the package label.

The second aspect of the present invention is simple user-request expression. The present invention not only uses the (machine-readable) programming information to program the scheduled events, but also uses it for users to express user requests (e.g., loading medication, refilling medication, modifying regimen for medication, deleting medication, taking medication, requesting user-compliance report, etc.) conforming to a user-request protocol where presenting the programming information to the programming-information reader in a predetermined manner indicates a specific user request. This method of user-request expression has not been suggested in the prior art and it has significant advantages: the entire user-input interface can be reduced to only a programming-information reader, and the users express user requests in extremely simple and consistent manner.

Given the fundamental idea of the user-request expression of the present invention, there are countless choices for the user-request protocol. One exemplary user-request protocol will be used in all descriptions of the preferred embodiment section: a single scan of the programming information indicates the request for taking a scheduled or emergency dose of a medication, a double scan (two consecutive scans within a preset period of time) indicates the request for loading (including refilling or modifying) a medication, a triple scan indicates the request for deleting a medication, and a quadruple scan indicates the request for a user-compliance report, etc. Preferably, the system produces a beep or other type of indication for each successful scan.

The processing unit 20 is programmed to detect the user requests according to the user-request protocol. The processing unit 20 only accepts valid and applicable user requests and takes predetermined actions according to the user requests. The processing unit 20 ignores invalid user requests (do not conform to the user-request protocol) and inapplicable (e.g., taking emergency dose or deleting a medication which is not in the system) user requests. This kind of user-request protocols is so easy to memorize, and a user can master it right away. However, since it is so simple and compact, it may be imprinted on the device for easy reference. Alternatively, the system may display or announce the user-request protocol to remind the user.

The prior art designs (including those utilizing machine-readable information) require the users to express user requests through conventional user-input interfaces consisting of buttons, keypads, touch screen, etc. No prior art design has such simple user-input interface as the present invention (a programming-information reader only). No prior art design allows users to express their requests in such simple and consistent way (scanning the programming information only). As a matter of fact, the prior art devices typically have user operation menus that a user has to learn and refer to, and they are usually too big to be imprinted on the device.

Simple user-input interface and simple user-request expression have significant implications. They not only reduce the physical complexity and components of the system, but also make the system much user-friendlier and easier to use. Furthermore, they reduce the operation errors. Complex user-input interface and elaborate user-request expressions are always accompanied with potential errors. With simple user-input interface and simple user-request expression, the present invention reduces potential error one step further.

It should be emphasized that using programming information to express requests sets the present invention apart from any prior art use of machine-readable information. In prior art use of machine-readable information, (1) the user is not given any choice; (2) scanning the machine-readable information only accomplishes one task, namely, conveying the encoded information to the system; (3) the system always acts the same way in response to the same encoded information. Using the Universal Product Code (UPC) as example, when a cashier scans the UPC barcode of a product, there is no choice given to the cashier about what he/she wants to do, the scan only conveys the encoded information (product identifier) to the system, and the system always fetches the price for the product and charges the customer. With the present invention, (1) the user is given multiple choices about what he/she wants to do; (2) scanning the programming information accomplishes two tasks, namely, it not only conveys the encoded programming information but also conveys the user request to the system; and (3) the system acts differently according to different user requests even though the encoded programming information is the same.

Different user request may require different programming information. If a user request requires programming the scheduled events (e.g., loading new medication, refilling, or modifying regimen for an existing medication), the programming information must contain the usage information (unless preloaded usage information is used, which will be described later). If a request needs to specify a medication, the programming information must contain the medication identifier. For other types of requests (e.g., taking a scheduled dose, requesting user-compliance report, etc.) where neither usage information nor medication identifier is required, the processing unit may be programmed to allow users to use any suitable programming information (e.g., any active programming information of the user, or programming information contains the user identifier) to make such requests. For the sake of simplicity, the description often simply states "scan/use the programming information" (for expressing a user request), which should be interpreted as "scan/use the programming information that contains proper information for the user request".

The third aspect of the present invention is the guided operation. For each user request, there are necessary operations that a user has to complete. For example, when user requests loading or deleting a medication, the user has to physically load the medication into, or remove the medication from the appropriate storage. Prior art systems leave their users alone to complete the user operations, where users have to identify the right medication, the right amount, and the right storage, etc. in order to complete these operations. The system of the present invention provides guidance to help the user to complete necessary operations corresponding to user requests. In addition to control signals for the scheduled events, the processing unit 20 also generates guiding signals corresponding to user requests. The guiding signals are sent to the controlled device 300. The controlled device takes appropriate actions in response to the guiding signals. The actions may include indicating the right storage, the right medication (identifier/name), and the right amount, etc., with a guiding means (or opening the access door of the right storage), to guide the user to complete the necessary operations. The guiding means generally refers to a device that can provide visual, audible, or tactile indication, or any combination of them. It may comprise displays (e.g., LCD screen), LEDs, buzzers, speakers, or vibrators. Most of the existing or conceived medication administering devices are equipped with such indicators, and the present invention can use them as the guiding means in addition to their original functions. The guiding signals may be used to drive the guiding means directly or used as commands/trigger signals.

The guided user operations not only simplify the user operations, making the system of the present invention much user-friendlier and easier to use than any prior art design, but also reduce the potential error associated with the prior art designs (such as loading a medication to a wrong storage, loading a wrong amount of medication, removing a wrong medication, etc.).

The fourth aspect of the present invention is automatic medication-storage mapping. Lacking a convenient medication-storage mapping, prior art designs require complicated manual operations, additional user programming, professional assistance, redundant components or devices, additional controls, or combination of them. The present invention achieves automatic medication-storage mapping by either combining it with guided loading or using sensors to detect where the medication is loaded. The first approach is that while guiding the user to load a medication to appropriate storage, the processing unit registers the storage with the medication (or the scheduled events). The second approach is that the user selects the storage to load a medication, the sensor detects the storage, and the processing unit registers the storage with the medication (or the scheduled events). Either way, the medication-storage mapping is automatically established without any additional user effort. Automatic medication-storage mapping not only overcomes the disadvantages of the prior art designs regarding this aspect, making the system of the present invention much simpler, user-friendlier, and easier to use than any prior art design, but also reduces potential error (e.g., registering a wrong medication or a wrong storage) associated with the prior art designs. The operation of the system of the present invention is described in the following.

When the user needs to load a medication (including refilling a medication, or modifying the regimen of an existing medication), he/she double scans the programming information, indicating request for loading. The processing unit firstly checks if the same medication has already existed in the system. There are three possible outcomes. The first one is that the medication does not exist (a new medication). The second one is that the medication exists and the programming information remains unchanged (a simple refill). The third one is that the medication exists but the programming information has changed (a refill with modified regimen or modifying regimen without refill). The processing unit finds appropriate storage: empty storage for new medication or the original storage for all other cases (simple refill, refill with modified regimen, and modifying regimen). The processing unit generates guiding signal (for loading, in this case) and sends it to the controlled device. The controlled device produces indication (e.g., indicating the appropriate storage compartment), or opens the access door (e.g., releasing an electromagnetically controlled latch, or using stepper motor) of the appropriate storage compartment. The user loads the medication as guided by the system (except for modifying regimen, no medication is actually loaded for that case). Of course, the programming information may carry a flag indicating new/refill/modifying. Anyway, user does not need to worry if he/she already has this medication in the system, what he/she has to do in different cases, or which storage to load the medication, but simply follows the guidance of the system. Since refilling and modifying are so similar to loading new medication, only "loading" is used and described in the following descriptions. The reader should keep in mind that loading also includes the other two cases.

The prior art devices typically require the user to provide further information (e.g., indicating new or refill, indicating the storage) and/or load the medication into appropriate storage, or otherwise the prior art systems may incorrectly treat a refill as a new medication and cause double dose.

The processing unit uses the programming information to program the scheduled events for the medication and stores them, if necessary (a simple refill of a medication with recurring scheduled events does not need to have the scheduled events re-programmed). The processing unit also establishes medication-storage mapping for new medication.

When a scheduled event (for the user to take medication) occurs, the processing unit generates control signals and sends them to the controlled device. The actions of the controlled device in response to the control signals may include: producing alarm, indicating the medication and unit dosage, indicating the storage compartment, tec. The control signals may be used to drive the appropriate sub-components of the controlled device or used as commands. The user scans the programming information once, indicating request to take the scheduled medication, and takes it. The processing unit may record the actual time that the user scans the programming information as user-compliance data.

Besides scheduled events, a user may request an emergency dose of a particular medication by scanning the corresponding programming information once. The processing unit recognizes the request for emergency dose since it is off schedule. The processing unit and the controlled device take the similar actions as for a scheduled dose, except that the alarm does not go off. The processing unit may be configured to skip the next scheduled dose or delay (reschedule) the remaining doses accordingly (this can also be directed by the programming information or user request). The programming information for some medications may indicate that no emergency dose is allowed or it is limited to certain amount, and the processing unit programs accordingly.

When the user needs to delete a medication (as directed by doctor), he/she triple scans corresponding programming information, indicating request for deleting. The processing unit may generate guiding signals (for deleting, in this case) and sends them to the controlled device. Depending on its capability, the actions of the controlled device may include: indicating the storage and/or opening the access door of the storage to guide the user to remove the medication, or dumping the (deleted) medication.

The system may also include an output device for user-compliance report (and/or outputting other information). The user quadruple scans the programming information, indicating request for user-compliance report. The processing unit generates a user-compliance report based on the scheduled events and the recorded user-compliance data, and outputs it in human-readable (printed) or encoded form (similar to the programming information). In the latter case, the programming-information reader may double as programming-information writer and reproduce the programming information. Providing user-compliance report is also a convenient way to inform or remind the caregiver how (starting date/time, schedule, and unit dose) and what medications the user is currently taking.

Figure 3:
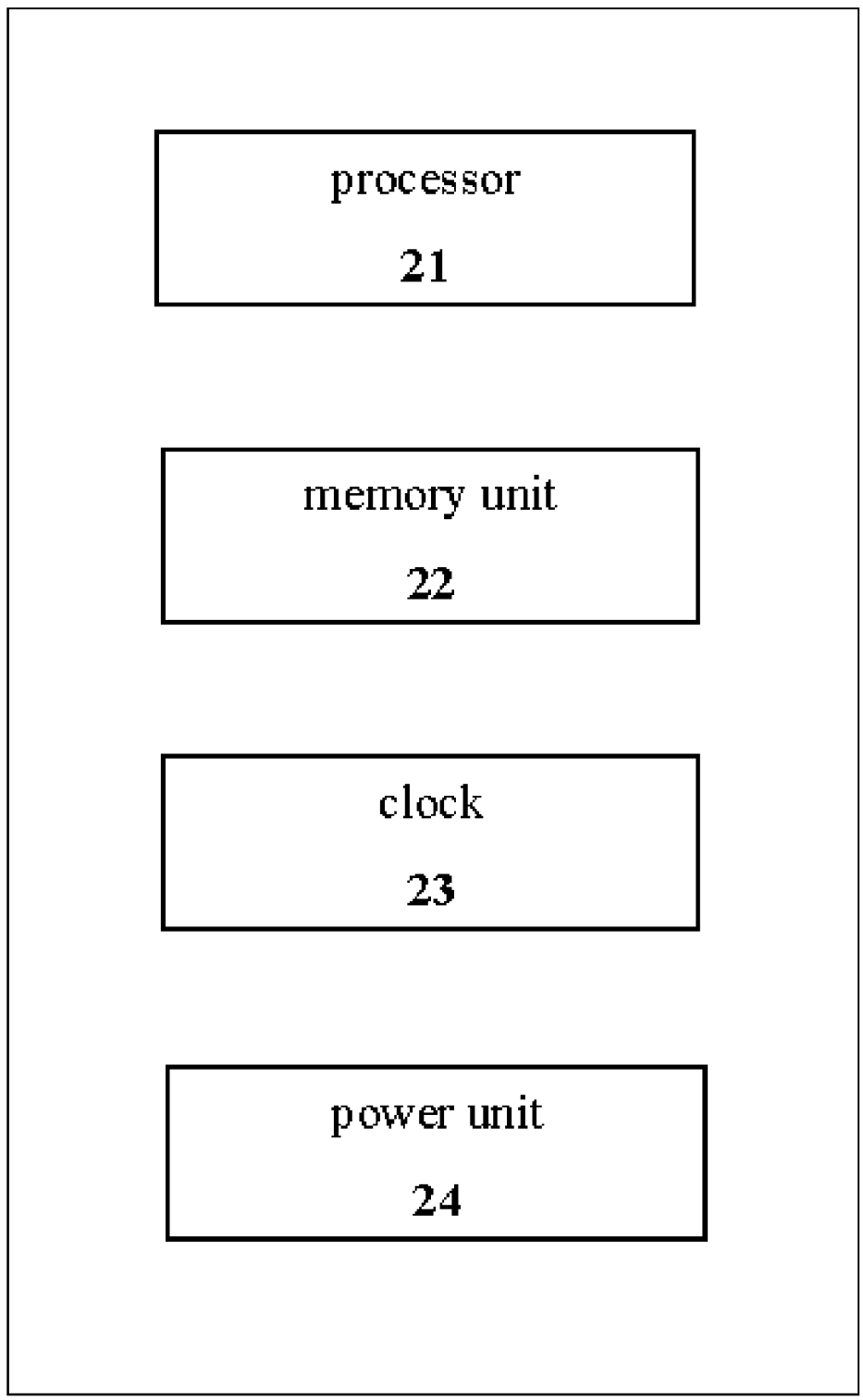
FIG. 3 shows the block diagram of the processing unit.

FIG. 3 shows the block diagram of the processing unit 20. The first characteristic of the processing unit of the present invention is that it interfaces with the programming-information reader rather than a conventional user-programming interface as for the typical prior art systems. The processing unit is capable of decoding the programming information from the programming-information signals (from the programming-information reader) according to the encoding protocol, and automatically programs the scheduled events id required. The second characteristic of the processing unit of the present invention is that it also detects the user requests from the programming-information signals according to the user-request protocol. The third characteristic of the control unit of the present invention is that in additional to generating control signals for scheduled events, it generates guiding signals to guide the user to complete the necessary operations corresponding to the user request. The forth characteristic of the processing unit of the present invention is that it automatically establishes medication-storage mapping without any additional user effort. The processing unit comprises a processor 21, a memory unit 22, a clock 23, and a power unit 24.

The processor 21 is mainly responsible for performing the above-described functions of the processing unit. It runs an embedded firmware that handles all functions of the processing unit.

The memory unit 22 may consist of both non-volatile (ROM and/or electrically erasable) memory and RAM to store the embedded firmware, programming information, scheduled events, medication-storage mapping, and other static and dynamic data.

The clock 23 keeps system time. Although in principle any suitable clock may be used, it is preferable that the user does not have to set the clock and the clock is not interrupted by power outage. It is often seen that the clocks of many household electronic devices (e.g., TV, VCR, stereo, microwave oven, telephone, fax machine) are not set or not set correctly, especially after a power outage. But having the clock of a medication administering device set incorrectly or interrupted by power outage could have devastating consequences. The fifth characteristic of the processing unit is that no clock setting (by user) is required. One choice is to have the clock set by manufacturer before shipment and keep it running (a pre-set clock, like many battery-driven watches, clocks, computers, and other electronic devices), so that user no longer needs to set clock. An alternative is to use a radio-controlled clock, which receives radio signal of standard time and automatically adjusts itself, hence eliminating the need of setting the clock. As a third alternative, the present invention proposes the use of a "relative-time" clock. A relative-time clock dose not necessarily keep the real time, but simply counts the elapsed time since the power is turned on. The user waits until it is time to take the first daily dose of a new medication (the user may elect to take the medication together with some other existing medications) to program the scheduled events (i.e., double scan the programming information). The processing unit uses that time as reference and programs the schedules events relative to it. In this way, the need of setting the clock is completely eliminated (not even by the manufacturer), and the clock starts working when the user starts the device.

Since there is no need to set the clock, the (user) clock-setting interface is no longer needed. Eliminating the clock setting and clock-setting interface reduces the complexity and components, making the system of the present invention user-friendlier and easier to use than any prior art system, and reduces the potential errors associated with the prior art designs (e.g., caused by incorrectly set or interrupted clock).

The power unit 24 provides power to the processing unit 20. Depending on the specific design, it may also provide power to the programming-information reader and/or the controlled device. The power unit 24 may include a backup power unit (e.g., with rechargeable batteries, photocells, capacitors) to keep the system running and maintain critical data (if they are stored in RAM) when the system is temporarily out of power. The backup power unit may further include a critical backup power unit that only keeps the clock running and maintains critical data as to last much longer (several months or even several years) without external power.

Most of the sub-components of the processing unit 20 can be integrated into an Application Specific Integrated Circuit (ASIC), or a general-purpose programmable microcontroller may be used to perform all or most of the functions of the processing unit.

The present invention can use almost all types of memory media to store the programming information. The preferred types of programming-information readers/carriers will be described in the following.

One embodiment of the programming-information reader is a barcode scanner, and the corresponding programming-information carrier is a barcode. This special barcode will be called programming-information barcode, in order to distinct it from any other barcode, such as the UPC barcode that identifies a product (manufacturer and product identifier).

Figure 2:
FIG. 2 shows one example of the programming-information carrier: programming-information barcode.

Use pharmacy-filled prescription as an example: when a pharmacist fills the prescription for a user, the pharmacist enters into the pharmacy's computer system the medication identifier (name) and the usage information along with other relevant information, such as doctor's information, user's information, insurance information, etc. There is no change in pharmacist's routine and equipment. The pharmacy can use any container or package suitable for the medication. Only the pharmacy's software takes an extra step: it encodes the medication identifier and the usage information into a programming-information barcode format according to an encoding protocol and prints it on the medication label. The medication label includes all other information as usual, as well as the programming-information barcode, as illustrated in FIG. 2. The software that generates the programming-information barcode can be an integrated component of the pharmacy's software or a separate software module provided by a third party.

If the medication label requires another barcode, such as the UPC barcode, the programming-information barcode may be marked, folded or provided separately to avoid confusion. Since the programming-information barcode has a specific signature, there is no actual interference. No particular position or orientation is required for the programming-information barcode, which does not even have to appear on the medication label or medication container, and can be provided separately.

The user takes home the medication, uses the programming-information barcode to express user requests, and follows the guidance of the system to complete the necessary user operations, as described previously.

Studies have shown that the error rate of barcode scanning is about 1 in 10 million. That is much lower than the error rate of human input (with a keyboard or similar user-input interface), which is about 1 in 100. So, the present invention virtually eliminates the programming error.

It is sufficiently clear from the above description that the programming-information barcode of the present invention differs fundamentally from other barcodes currently used or proposed in prior art. The barcodes used in prior art are mainly for identification purposes, such as to identify a person (patient or caregiver), a medication (name, source, lot number, expiration date, etc.), or internal use to identify an order, a storage unit, etc. For example, the FDA rules use of barcodes in the healthcare facilities to match the patient with the prescribed medication for that patient. Although the barcode on the package of unit-dose medication, which ensures the five rights (right patient, right drug, right dose, right route, and right time), contains unit dosage and time information, it is not used for programming medication administering devices or user-request expression, but for verifying whether the unit dose matches the medication record for the patient in the database. Of course, the present invention can extend the programming-information to incorporate further information (such as user identifier) for additional purposes, if deemed useful or necessary.

Another embodiment of the programming-information reader is a magnetic card reader, and the corresponding programming-information carrier is a magnetic card (similar to a credit card reader and the credit card pair). In this case a paper or plastic card with both human-readable information and a magnetic strip that encodes the programming information may be used instead of the medication label. The method of use is very similar to that of programming-information barcode.

Yet another embodiment of the programming-information reader is a radio-frequency (RF) tag receiver, and the corresponding programming-information reader is a RF tag. In this case, the pair communicates wirelessly via radio waves. Preferably, the RF tag has a low transmission range, so that it can only be read in the proximity of the receiver.

Yet another embodiment of the programming-information reader is a smart card reader, and the corresponding programming-information reader is a smart card. Smart card has embedded IC and memory. The IC of a smart card may have sufficient processing power to do more than just providing memory, e.g., taking some or even full functionality of the processing unit. In such case, the programming-information carrier (external component), the programming-information reader, and the part of, or the entire processing unit, are physically integrated in the smart card (detailed description of this embodiment will be given later).

In order to store large amount of programming information, e.g., complicated programming information or with additional information, 2D barcodes can be used. Magnetic strip (with multiple tracks) and smart card usually have large capacity, and are erasable and re-writable. Re-writable programming-information carriers allow the programming information to be modified. So, the programming information can be updated and these carriers can be reused. Furthermore, new information, such as user-compliance information, can be added. When using a re-writable programming-information carrier, such as magnetic card or smart card, the output device and the programming-information reader can be combined to form a machine input/output interface. This machine input/output interface not only reads the programming information from the programming-information carrier but also writes the (encoded) user-compliance report (and perhaps other information) back to it.

The method and control unit of the present invention can be adopted to control any type of medication administering system or device, and all typical types of such devices, as well as the corresponding methods of guided user operations and automatic medication-storage mapping, will be described in the following.

Figure 4A:
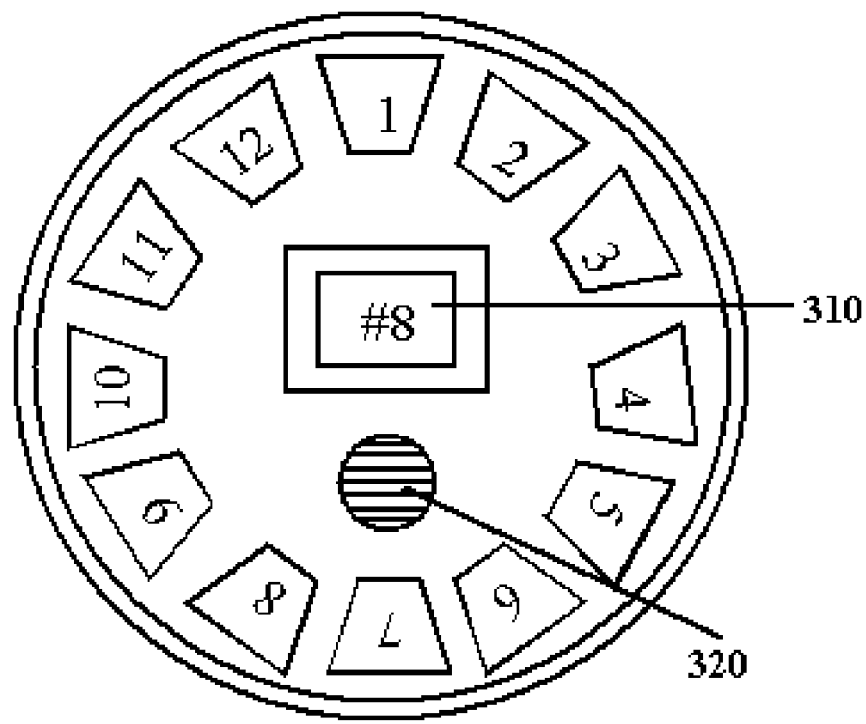
FIG. 4A shows one exemplary application of the present invention: a dose-compartment medication organizer with indicator.

One example of the controlled device is a dose-compartment medication organizer with an indicator. In this case the system works as a dose-compartment medication organizer with auto-programming medication reminder. FIG. 4A shows the top view of the system. In this exemplary configuration, the programming-information reader (on the sidewall of the device, not seen in this top-view figure), the processing unit, and the controlled device are all integrated into one physical unit. The dose compartments are labeled from 1 to 12.

As mentioned previously, it is difficult to load medications to, add new medication, or delete medications from the prior art dose-compartment medication organizers and dispensers. That can be demonstrated by a simple example. Suppose that a user has to take two tablets of medication A every two hours, one tablet of medication B every three hours, and one tablet of medication C every five hours. With the prior art systems, the user has to figure out the following loading-scheduling plan, load the medications, and program the scheduled events accordingly (notice that the time intervals are not uniform):

| Compartment number | Unit dosage | schedule |
| --- | --- | --- |
|  | 2A, 1B, 1C | 0 hours |
| 1 | 2A | 2 hours |
| 2 | 1B | 3 hours |
| 3 | 2A | 4 hours |
| 4 | 1C | 5 hours |
| 5 | 2A, 1B | 6 hours |
| 6 | 2A | 8 hours |
| 7 | 1B | 9 hours |
| 8 | 2A, 1C | 10 hours |
| 9 | 2A, 1B | 12 hours |
| 10 | 2A | 14 hours |
| 11 | 1B, 1C | 15 hours |
| 12 | 2A | 16 hours |

This loading-scheduling plan is oversimplified, since it ignores the constraints of total daily dosage of each medication, and the user probably does not want night schedules. Figuring out even such an oversimplified loading-scheduling plan requires some skill and brainwork from the user, and it can be quite difficult or even prohibitive for some users, especially vision-impaired users. Loading subsequent rounds is even more difficult since the user has to remember the previous round in order to continue. Due to this severe problem, the prior art dose-compartment medication organizers and dispensers practically are used to manage medications with extremely simple schedules, such as a few times everyday with uniform intervals.

The present invention provides a solution to this problem: guided user operation. With the present invention, the user simply double scans the programming information of all medications one after another within a predetermined period of time (e.g., one minute), indicating request for loading several medications. The processing unit automatically figures out the loading-scheduling plan and guides the user to load the medications. For example, the display 310 may show a message like this: 2 A: 1, 3, 5, 6, 8, 9, 10, 12; 1 B: 2, 5, 7, 9, 11; 1 C: 4, 8, 11. This means to load 2 tablets of medication A into dose compartment 1, 3, 5, 6, 8, 9, 10, and 12, and so on. In the case where each dose compartment has its own indicator (LED), the message may simply be: 2A, and the LEDs of compartment 1, 3, 5, 6, 8, 9, 10, 12 are flashing. This means to load 2 tablets of medication A into every dose compartment with flashing LED. When the user finished loading medication A, he/she scans the programming information (can be any of them) and the processing unit guides the user to load other medications. Alternatively, the processing unit may be configured to guide the user to load the dose compartments (instead of medications) in sequence. The display may show a message like: 1: 2A, 2: 1B, 3: 2A, etc. in sequence, just as the above loading/schedule plan. In the case where dose compartments have their own LED indicators, the display shows 2A and the LED of dose compartment 1 is flashing, and so on. There are many other similar ways to guide the user to load the medications.

While guiding the user to load the medication, the processing unit also establishes the medication-storage mapping automatically without any additional user effort. For dose compartment medication organizer (dose-compartment medication dispenser or pre-packaged medication organizer/dispenser), the processing unit actually registers scheduled events (instead of medication) with the storage (dose compartments). The processing unit can easily handle total daily dosage and skip night schedules. Loading subsequent rounds is just as easy since the processing unit remembers the previous round and guides the user to continue.

This example manifests the fundamental difference between the prior art systems and the system of the present invention. The prior art systems tell their user: "Figure out the loading-scheduling plan, follow your plan to load the medications, and tell me (enter through user programming interface) the scheduled events and the medication-storage mapping". While the system of the present invention does the opposite: "I have figured out the loading-scheduling plan for you, follow my guidance to load the medications, and I will take care of the scheduled events and the medication-storage mapping".

When the user needs to load a new medication to an already loaded system, he/she double scans the corresponding programming information, indicating request for loading. If the schedule of the new medication is compatible with those of the existing medications, the processing unit will guide the user to load the new medication into the appropriate dose compartments. In the case that the schedule of the new medication is not compatible with those of existing medications, the processing unit will guide the user to reload all medications. Since the system of the present invention provides guided user operations, the reload is no longer a daunting task.

Figure 4B:
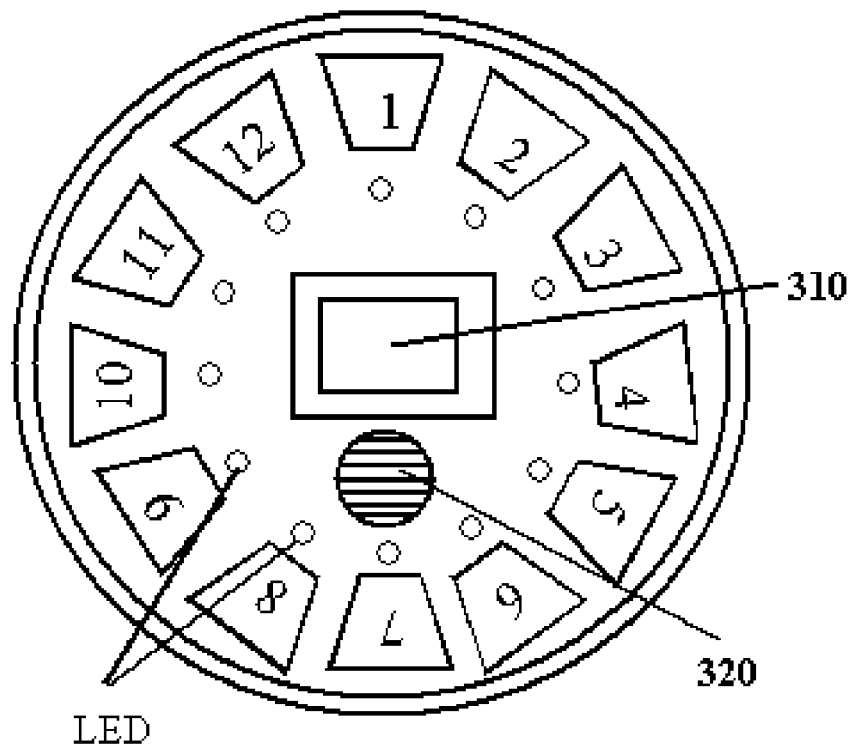
FIG. 4B shows another exemplary application of the present invention: a dose-compartment medication organizer with multiple LEDs, each for a dose compartment.

When a scheduled event occurs, the display 310 of the indicator indicates the corresponding dose-compartment number (e.g., dose-compartment #8 as shown in FIG. 4A), and the alarm 320 sounds. The user scans the programming information once (which stops the alarm) and takes the medication. The processing unit records the actual time when the programming information is scanned as user-compliance data. Of cause, each dose-compartment may have its own LED, as shown in FIG. 4B.

The user uses the programming information for all other requests, conforming to the user-request protocol described previously. For emergency dose, the actions of the processing unit and the controlled device are very similar to those for scheduled dose, except that the alarm does not go off. For this example, the next scheduled dose is automatically skipped (the user has already consumed it). For deleting a medication, the processing unit deletes the scheduled events for that medication (if they exists alone), and the indicator indicates all dose compartments containing that medication to guide the user to remove them.

Yet another example of the controlled device is similar to the above one, except that the dose compartment medication organizer has multiple magazines, each having multiple dose compartments in turn. This embodiment is suitable for medications with very different or very complex schedules. Of course, once can always use one magazine for each medication, but such arrangement results inefficient storage. On the other hand, it is impractical to ask a user to figure out an optimal loading-scheduling plan that groups the medications into magazines to achieve the most efficient storage and programming. With the present invention, the processing unit automatically groups the medication with compatible schedules into the same magazine and figure out the loading-scheduling plan for each magazine. All operations are very similar to those of the example immediately above except magazine number (identifier) should also be included in programming. Since a new medication with incompatible schedule can always be added with a new magazine, the existing medications no longer have to be reloaded.

Figure 5A:
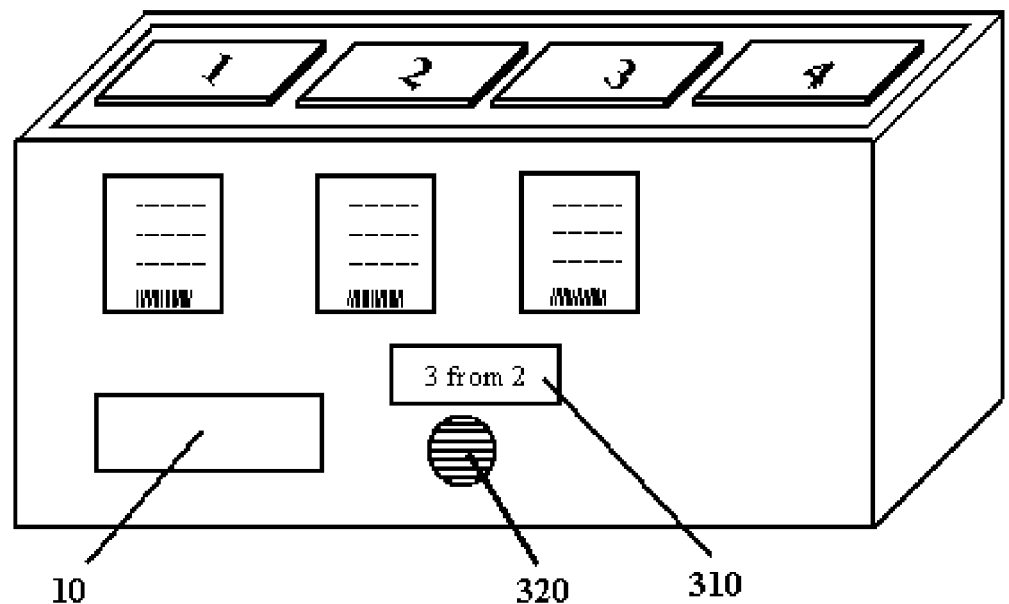
FIG. 5A shows yet another exemplary application of the present invention: a bulk medication organizer with an indicator.

Yet another example of the controlled device is a bulk medication organizer with an indicator. In this case the system works as a bulk medication organizer with auto-programming medication reminder, as shown in FIG. 5A. In this exemplary configuration, the programming-information reader, the processing unit, and the controlled device are all integrated into a console.

When the user needs to load a medication, he/she double scans the programming information, indicating request for loading. The processing unit finds appropriate compartment and the corresponding compartment number is displayed on 310 and/or the corresponding access door opens, and the user loads the medication into the compartment. The processing unit programs the scheduled events if necessary. The medication-storage mapping is automatically completed without any additional user effort. An alternative method for automatic medication-storage mapping is to install a sensor (a simple micro switch will do) on each access door. Instead of guided by the system, the user chooses appropriate compartment and loads the medication. The sensor detects the compartment (the access door has been opened and closed) and the processing unit establishes the medication-storage mapping. The user may optionally transfer the human-readable medication label to the corresponding compartment for easy visual comprehension, as depicted in FIG. 5A.

When a scheduled event occurs, the display 310 shows the storage compartment number and the unit dosage (e.g., 3 tablets from compartment number 2, as shown in FIG. 5A) and the alarm 320 sounds. The user scans the programming information once (the access door of compartment 2 may open) and takes the medication. The processing unit records the actual time when the programming information is scanned as user-compliance data.

The user scans the corresponding programming information for requesting an emergency dose of a medication. The actions of the processing unit and the controlled device are similar to those for scheduled dose, except that the alarm does not go off. The user triple scans the programming information for deleting a medication, the corresponding compartment number is displayed and/or the access door of the corresponding compartment opens, the user empties that compartment, and the processing unit deletes the corresponding scheduled events.

Figure 5B:
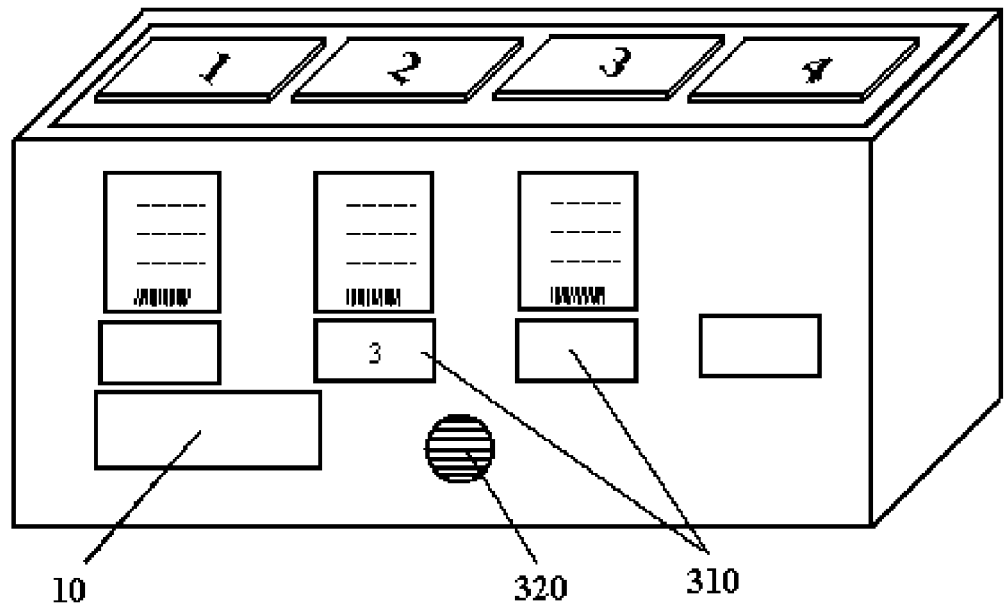
FIG. 5B shows yet another exemplary application of the present invention: a bulk medication organizer with multiple displays, each for a compartment.

Yet another example of the controlled device is a bulk medication organizer with multiple displays 310, each for a compartment, as shown in FIG. 5B. This case is very similar to the example immediately above, except the displays no longer need to display the compartment number.

Figure 6:
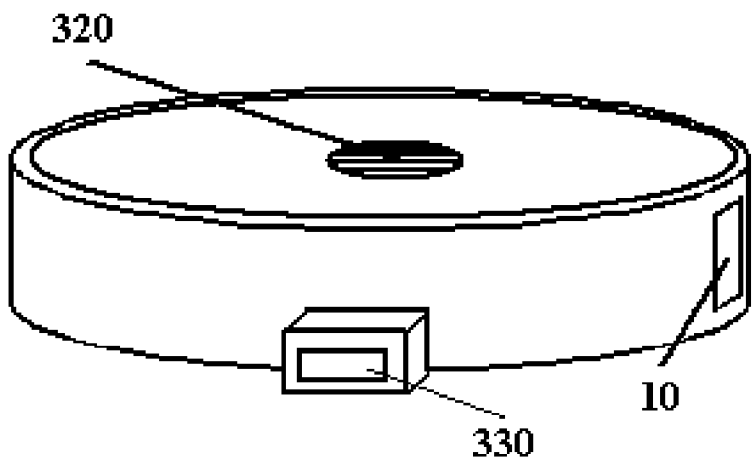
FIG. 6 shows yet another exemplary application of the present invention: a dose-compartment medication dispenser.

Yet another example of the controlled device is a dose-compartment medication dispenser with an alarm. In this case, the system works as an auto-programming dose-compartment medication dispenser. In this exemplary configuration, the programming-information reader, the processing unit, and the controlled device are integrated into one physical unit, as depicted in FIG. 6. All operations are similar to those of the dose-compartment medication organizer, except the scheduled and emergency dose are dispensed from the outlet 330.

Yet another example of the controlled device is similar to the above, but the dose-compartment medication dispenser has multiple magazines to handle medications with very different and complex schedules. For this embodiment, both the magazine and dose compartment number are displayed. All operations are similar to those of the above example.

Figure 7A:
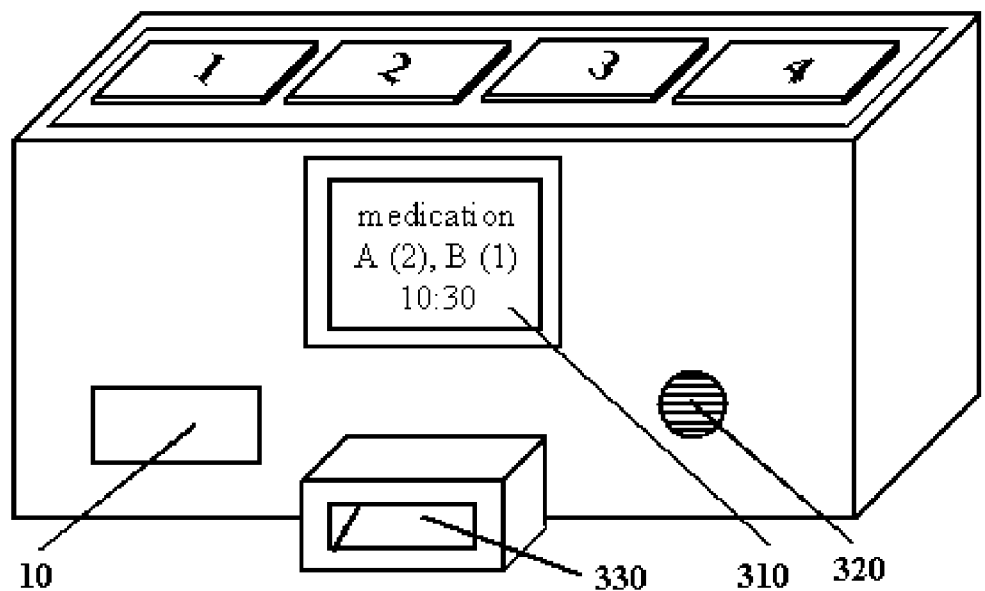
FIG. 7A shows yet another exemplary application of the present invention: a bulk medication dispenser.
Figure 7B:
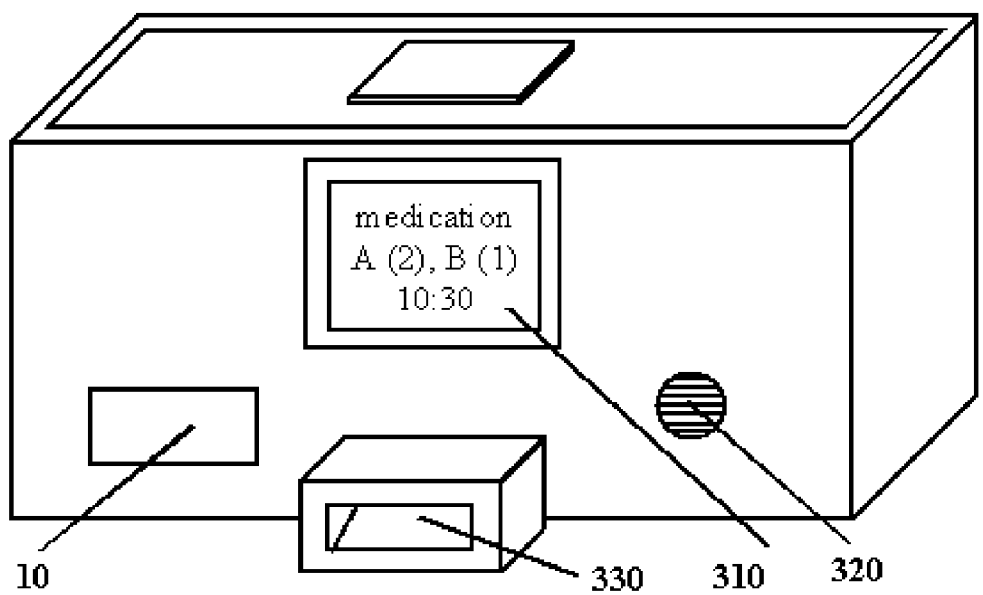
FIG. 7B shows yet another exemplary application of the present invention: a bulk medication dispenser with a common access door.

Yet another example of the controlled device is a bulk medication dispenser. In this case the system works as an auto-programming bulk medication dispenser. In this exemplary configuration the programming-information reader, processing unit, and the controlled device are integrated into one physical unit. Each storage compartment may have its own access door (labeled 1 to 4) as depicted in FIG. 7A, or they share a common access door (depicted in FIG. 7B) that can be selectively docked (automatically controlled by the processing unit) to a storage compartment inside the device. For this embodiment the programming information must include the medication identifier (name). This embodiment is fully automatic, yet programming free.

When user needs to load a medication, he/she double scans the programming information, indicating request for loading. The processing unit selects the appropriate compartment. The number of the selected the compartment is displayed on 310, and/or the corresponding access door opens. For the configuration in FIG. 7B, the processing unit docks the common access door with the selected compartment, and the common access door may open. The user loads the medication as guided by the system. For either configuration, the medication-storage mapping is automatically established without additional user effort. The processing unit programs the scheduled events if necessary. All operations are similar to those of bulk medication organizer, except that the scheduled and emergency doses are automatically dispensed and the deleted medications are automatically dumped.

Figure 8:
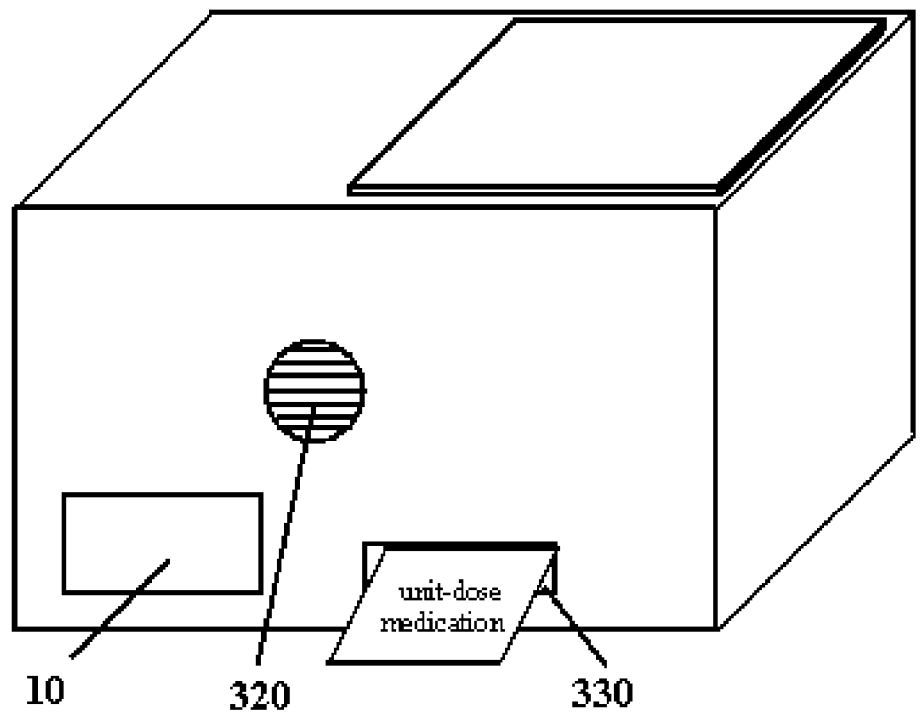
FIG. 8 shows yet another exemplary application of the present invention: a prepackaged medication dispenser.

Yet another example of the controlled device is a prepackaged medication dispenser with an alarm, as shown in FIG. 8. In this case, the system works as an auto-programming prepackaged medication dispenser. In this exemplary configuration the programming-information reader, processing unit, and the controlled device are integrated into one physical unit. Except the medications are prepackaged (unit-dose packages are dispensed through outlet 330), the operations are similar to those of dose-compartment medication dispenser.

Yet another example of the controlled device is similar to the above, but the prepackaged medication dispenser has multiple magazines to handle medications with very different and complex schedules, or prepackaged medications from different providers. When the user needs to add a magazine, he/she double scans the programming information associated with the magazine, indicating request for loading. The processing unit selects and indicates an available (empty) mounting rack to guide the user to mount the magazine. The medication-storage mapping is automatically established without any additional user effort. The user uses programming information for all other requests, conforming to the user-request protocol described previously. For emergency dose, the system dispenses a unit dose from the appropriate magazine. For deletion, the system deletes the corresponding scheduled events and indicates the magazine to guide the user to remove it. Of course, sensors (such as micro switches) may be used to detect which mounting rack a magazine has been mounted to or removed from, allowing the control unit to establish medication-storage mapping automatically.

With automatic programming and guided user operations, the system of the present invention is so easy to use and there is no genuine need for a user to have medications prepackaged. These examples of prepackaged dispenser simply illustrate that the present invention can be applied to all types of devices, simplify their structures (user-input interface), and improve their usability.

Yet another example of the controlled device is a modem or other communication device that can communicate with a number of remote devices. The desired functions for the communication device may include: sending voice or text message for each scheduled event to remind the user to take medication, reporting incompliance event, or any other problem, or that the inventory of a medication is below a predetermined threshold, to designated person. The designated phone numbers may be encoded in the programming information and read into the system when the medication is added. In this case the programming-information reader, the programming processing unit, and the controlled device may be integrated into one physical unit. When a medication is finished or deleted, the processing unit deletes the corresponding scheduled events and the designated phone number.

Yet another example of the controlled device is a PC. The control unit communicates with the PC through a cable or wirelessly (RF, infrared, etc), and the PC may in turn control other devices, or communicate with remote computers through Internet. A special application runs on the PC takes appropriate actions in response to the signals that the control unit transmits.

The last two embodiments may be configured to have the capability of downloading programming information from the remote device (or computer) to the local device. This is especially useful when doctor changes the medication regimen for the user. This differs from the remote-controlled dispensers of the prior art in that the scheduled events are programmed locally and automatically as opposed to being programmed remotely and by healthcare professionals. Furthermore, the communication device needs to be connected and communication channel needs to be setup only when downloading the programming information, as opposed to constantly connected and setup for receiving control signals as required by the prior art remote-controlled methods.

The alarm in the above descriptions may be replaced (or complemented) with a visual indicator (e.g., LED) or a vibrator to produce visual or vibration alarm. Similarly, the visual display may be replaced (or complimented) with a speaker, which announces pre-recorded or synthesized voice messages. Examples include: "please take three tablets of medicine xyz", "please take the medication in dose-compartment number eight of magazine number two", "please load medication into/remove medication from compartment three", and "please load two medication A, one medication B, and one medication C into dose compartment number eight of magazine number one".

As an alternative to the method described above, the processing unit may have preloaded usage information with medication identifier for common medications. For definiteness, these two methods will be referred as the method of the encoded usage information and the method of preloaded usage information. With preloaded usage information, the programming information only needs to contain a medication identifier. One example is to use the manufacturer and product identifier encoded in the UPC barcode of a medication as the medication identifier. Another example is to use the National Drug Code (NDC) of a medication as the medication identifier (NDC barcode will be available on medication packages in the future).

The user scans the programming information that contains the medication identifier (e.g., UPC barcode or NDC barcode) to express user requests, conforming to user-request protocol described previously, and the programming-information reader reads and converts it into appropriate programming-information signals. The processing unit decodes the medication identifier from the programming-information signals. If necessary (programming the scheduled events is required), the processing unit searches the preloaded usage information with matching medication identifier and uses the corresponding preloaded usage information to program the scheduled events.

Similar to the encoded usage information, the preloaded usage information may contain directly the scheduled events. In that case, programming and deleting the scheduled events simply means activating and deactivating them, respectively. The method of preloaded usage information is particularly suitable for non-prescription medications (OTC, dietary supplements, etc.). If NDC or other unique medication identifier is used, each preloaded usage information maps to a single medication identifier. If UPC or other non-unique medication identifier is used, each preloaded usage information maps to multiple medication identifiers (they all identify the same medication). The processing unit can be easily programmed to accept multiple types of medication identifiers. Therefore, the method of preloaded usage information of the present invention is very flexible.

Figure 9:
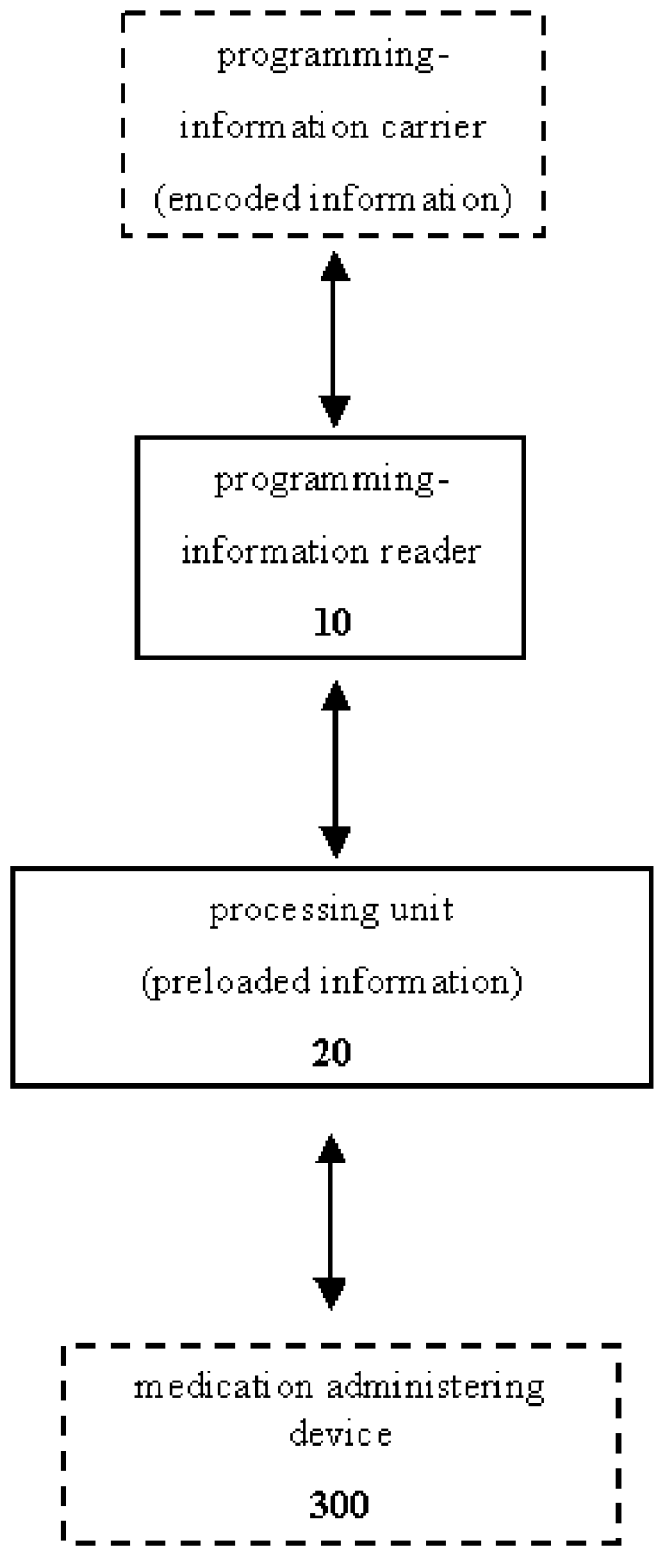
FIG. 9 shows the system of present invention using both encoded and preloaded usage information.

The method of preloaded usage information can be used separately or in conjunction with that of encoded usage information. Actually, the method of encoded usage information and preloaded usage information represent two extremes. In the most general case, the programming information may have entire or part of the information, and the preloaded information may contain entire or part of the information. The processing unit selectively uses them to complete the user request, according to a predetermined rule (e.g., the encoded information has precedence). FIG. 9 shows the block diagram of the system of the present invention with the general method.

The processing unit may also have preloaded medication-interaction information for common medications (especially suitable for the method with preloaded usage information). When the user loads a new medication, the processing unit checks the new medication against the existing ones for potential interactions, and warns the user (e.g., sounds alarm, display warning message), or even refuses to load the new medication, if interactions exist. Of course, such interaction information may also come with the programming information for medications having known strong interaction, provided a large capacity carrier is used. This provides an additional layer of safeguard.

U.S. Pat. Nos. 5,088,056, 4,970,669, 4,942,544, 4,837,719, 4,831,562, and 4,682,299 proposed medication reminders with preloaded schedule information for common medications, but these prior art designs all require a piece of code that contains the starting memory address of the schedule information of a medication in order to retrieve it. This method is quite cumbersome, because it requires that the medication manufacturers and medication providers know how the device manufacturer stores the schedule information for each medication in order to be able to provided the memory address code. Unless the medication provider is also the device manufacturer, this prior art method calls for an organization similar to the Uniform Code Council (UCC, in charge of UPC) to coordinate with the medication providers and the device manufactures. UCC only needs to assign unique manufacturer identifier to each manufacturer (which in turn assigns product identifier and makes up the UPC for each product it produces), this organization has to assign unique memory address to each medication. Furthermore, it would be very difficult to update the preloaded scheduled events, add new ones, or change the design, since that would likely change the memory addresses.

The present invention (with preloaded usage information) does not have any of these problems. There is no need for medication providers to provide any extra code, since the UPC barcodes are already provided on the packages for almost all medications (NDC barcodes are coming). The preloaded usage information can be updated and the new ones can be added freely, since the matching is based on the medication identifier as opposed to the memory address. Furthermore, scanning the medication identifier of the present invention also accomplishes the user-request expression. All other operations with the method of preloaded usage information are almost identical to those with the method of encoded usage information.

Figure 10:
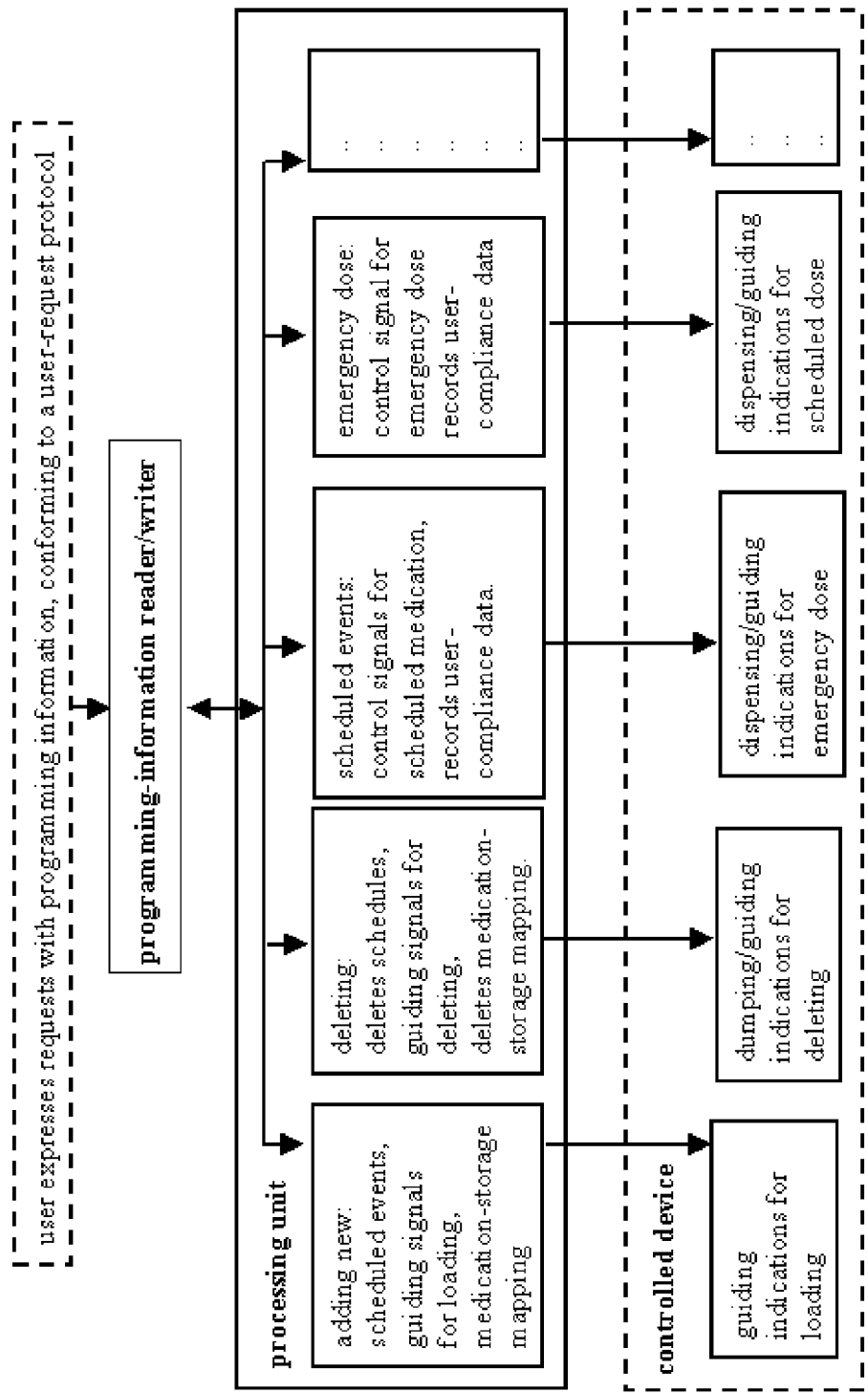
FIG. 10 summarizes operations of the system of the present invention.

The operation of the system of the present invention is summarized in FIG. 10. The user expresses desired request by presenting the programming information to the programming-information reader in a predetermined manner, conforming to the user-request protocol. The processing unit detects and determines the user request according to the user-request protocol. The processing unit takes predetermined actions according to the user requests. The processing unit also decodes the programming information according to the encoding protocol.

For loading (including refilling and modifying), the processing unit programs the scheduled events selectively using the encoded information and preloaded information, if required (for new medication or new usage information). The processing unit may further generate guiding signals (for loading, in this case). The actions of the controlled device in response to the guiding signals may include indicating the storage, indicating the medication, indicating the amount of medication, and opening the appropriate access door, to guide the user to load the medication. The processing unit may further establish the medication-storage mapping automatically.

For deleting a medication, the processing unit deletes the scheduled events for the medication and the medication-storage mapping (if applicable). The processing unit may further generate guiding signals (for deleting, in this case). The actions of the controlled device in response to the guiding signals may include indicating the storage, indicating the medication, indicating the amount of medication, and opening the appropriate access door, to guide the user to remove the medication, or dumping the deleted medication.

For each scheduled event, the processing unit generates control signals. The actions of the controlled device in response to the control signals may include: producing (visual, audible, tactile) alarm, indicating the medication identifier (name), indicating the unit dosage, indicating the storage, dispensing the medication.

For emergency dose, the actions of the processing unit and the controlled device are similar to those for scheduled dose, except that the alarm does not go off. The processing unit may be configured to skip the next scheduled dose or delay the remaining doses.

If the user requests a user-compliance report, the control unit generates one based on the scheduled events and the recorded user-compliance data (some type of indication of medication consumption). Other desired functions may be included, and the corresponding operations generally follow the same pattern. The system may further comprise an output device for user-compliance report or other information. If a rewritable memory media is used, the programming-information reader may be combined with the output device (which may be called as the programming-information writer).

Differing from prior art use of machine-readable information where the machine-readable information is used only for one task (users are not given choice to make request), in the present invention the programming information is used not only for uses to express user requests but also for the processing unit to complete various types of user requests. For example, programming the scheduled events, dispensing emergency dose, and deleting medication all require using entire or part of the programming information. After loading the medication, the user should keep the programming-information carrier for later use. Of course, other controls may be used as alternative ways for user-request expression (explained later). It should be emphasized that the present invention does not require the programming information carrier always be inserted into, or accurately aligned, or in stringent contact with any other component of the system. Nor is the programming-information carrier to be affixed to the medication package with precise location and orientation. In fact, it can be carried and kept separately from the system and medication. This kind flexibility is one of the advantages of the present invention over the prior art designs.

From the above descriptions, it is clearly seen that the system of present invention automatically programs the scheduled events, has the simplest user-input interface (programming-information reader), allows users to express user requests with extremely simple manners (scanning programming information), incorporates guided user operations, establishes medication-storage mapping automatically, and requires no clock setting. The system of the present invention is much easier and more intuitive to use than any prior art system, hence, it can be used by a much broader range of users. To further assist vision-impaired users, physical confinements or marks recognizable by touch can be added on the programming-information carrier and the programming-information reader to assist their alignment, so that a vision-impaired user can scan the programming-information easily. Braille or other symbols may also be provided instead of, or in addition to normal text on programming-information carriers and the devices. Furthermore, to guide the vision-impaired users to load, take, or delete medication, tactile indicators (e.g., small vibrators) may be added to each storage compartment or container, and a speaker may be used instead of, or in addition to a visual display.

ALTERNATIVE EMBODIMENTS

It should be understood that the preferred embodiments described in the preceding section serve only as examples. Based on the fundamental idea and the spirit of the present invention, various alternative embodiments can be readily designed.

In the preferred embodiment section, it is described that the programming information contains the usage information (or scheduled events) and/or medication identifier. Obviously, additional information can be added for more detailed programming or for other enhancement. For example, the medication's expiration date may be included, and the system later warns the user of expired medication or takes other actions, such as deleting the scheduled events and dumping the expired medication. The total amount of each loaded batch of medication may also be included in the programming information, so that the system can track the consumption of that medication and reminds the user to refill when the inventory is below a predetermined threshold. Of course, sensors may be employed to detect the actual inventory of each medication. The programming information may also contain a remind date/time for refilling so that it can be programmed to remind the user. If the medication inventories are tracked, the processing unit may be programmed to delete the recurring schedule event of a medication when the medication is finished.

Additional (secondary) usage information for a medication, such as "taking plenty of water" or "taking before/with/after a meal", can also be included in the programming information. The system may display or broadcast such special instructions when the user takes the medication. The programming information may also include the type of the medication (e.g., blood-pressure control, antibiotics, cholesterol control, etc.) to inform the user. The programming information may even include an image of the medication to help user to identify it (for example, when deleting a medication from a dose-compartment medication organizer/dispenser).

The programming information may also include tolerance in schedule (e.g. plus/minus 1 hour), unit dosage (e.g. plus/minus 1 tablet), and total daily dose (e.g. plus/minus 1 unit dose), so that the processing unit may program (group) several medications for the user to take together (within their tolerances). The programming information may indicate a medication as "take as needed". For such medication, the processing unit only programs the unit dosage without the schedules, and the user requests it just as requesting an emergency dose.

In the preferred embodiment section, several (preferred) embodiments of the programming-information carrier/reader pair are described: barcode/barcode scanner, magnetic card/magnetic card reader, RF tag/RF tag receiver, smart card/smart card reader. Additional examples for programming-information carriers may include diskettes, portable hard disks, flash memory, CDs, magnetic tapes (cassettes), optical (holographic) memory devices, biologic memory devices, etc (with corresponding readers). Any suitable technology and device, presently existing or developed in the future, may be used, as long as it is capable of carrying and allowing the recovery of the programming information. Unusual carrier/reader pairs include image/digital camera, music box/microphone, where the pixels of the image and the tones of the music encode the programming information. The communication between the pair (carrier and reader) can be electrical/electronic (plugged), optical/infrared (e.g., like a television remote control), radio, mechanical (e.g., vibration with specific patterns), sound (including infrasound and ultrasound). The programming-information carrier/reader pair may be integrated, for example, a memory device that outputs programming-information signals directly to the processing unit.

In the preferred embodiment section, it is described that the programming information is machine-readable. That does not exclude programming information that is also human-readable or human-comprehensible. For example, ordinary text medication label could be used as programming-information carrier if the programming-information reader is a scanner supported by a character-recognition system (implemented in the processing unit). Another example is a recording device (programming-information carrier) that carries recorded human-voice information (programming information) and a sound-receiving device (programming-information reader) such as a microphone, supported by a human-voice recognition system. With this embodiment, even a person that dictates the human-readable usage information (the programming information) plays the role of a programming-information carrier. Notice that even human-comprehensible programming-information is considered "encoded" since it must follow a predetermined format (encoding protocol) in order to be interpreted correctly. Furthermore, encoding usually reduces memory space.

In the preferred embodiment section, the programming information is described as one piece, e.g., a whole barcode. It is possible to divide it into more granular forms. For example, one piece for time/schedule, e.g., twice a day, one piece for unit dosage, e.g., three tablets, each with a special "signature" indicating its type.

In the preferred embodiment section, it is described that the programming information comes with the medication. Some medications (in particular OCT and dietary supplements) with standard schedules and dosages can use pre-made templates. For example, the user can use a label with both printed text "twice a day with one tablet" and a programming-information barcode encoded with the same information to program the scheduled events for a suitable medication. A user can also combine several pre-made granular templates, e.g., one encoded with "8:00 AM", one encoded with "two tablets", to make up a desired programming information. Pre-made template is particularly helpful if the medication provider (pharmacy, mail-order, manufacturer, etc.) does not provide the programming information. A booklet of various pre-made (granular) templates may be provided with a medication administering device (that incorporates the present invention), so that the user can make up almost any regular (not too complicated) programming information. For some embodiments, medication identifier is not required, pre-made templates are sufficient. The control unit simply registers and refers medications as A, B, C, D, etc. Otherwise, pre-made templates can be used with another piece of programming information that contains the medication identifier, such as UPC or NDC. A booklet of pre-made templates that contains common medication identifiers may also be provided for use with preloaded usage information.

Programming information may also be transmitted remotely via electronic means that are commonly available, e.g., transmitting a programming-information barcode via facsimile, or through Internet, e.g., attaching a programming-information barcode file to email. Programming information, especially pre-made templates, can also be provided (by medication manufacturers, healthcare facilities, or qualified organizations) on web site for user to download. Again, remote transmission of programming information differs fundamentally from the remote control methods of prior art. Here, the scheduled events are programmed locally and automatically, and the remote communication is only needed when downloading the programming information.

In the preferred embodiment section, it is described that for Rx medications the programming-information is provided by the prescription-filling facility. The process may start from the prescription generator, e.g., doctors in clinics and hospitals. When a doctor prescribes a medication for a user, the doctor's computer generates the programming information (with additional information if necessary) and loads it into a programming-information carrier. The programming information may be used by the prescription-filling facility to fill the prescription (total quantity of medication must be included).

Studies have shown that miscommunication between doctors and prescription-filling facilities contributes a significant percentage to the total prescription error. Using programming-information carrier through the entire process, from prescribing the medication to programming the user device, the present invention virtually eliminates all potential errors that exist for the prior art methods.

In the preferred embodiment section, it is described that each medication has a programming-information carrier that carries the programming information for that medication. In fact, it is possible to use a single programming-information carrier for multiple medications. In particular, a reusable form of such carrier is a re-writable card (e.g., magnetic card or smart card) that contains programming information of all medication that a user is currently taking, or even contains history information, as long as the storage allows it and such information is deemed useful or necessary. The user carries this card when he/she sees a doctor. The doctor can retrieve or update the information, such as obtaining user-compliance report, modifying the regimen, prescribing new medication, or deleting a medication. Each medication in the card may have a pharmacy flag and a user flag. The doctor's computer sets the flags to indicate a new medication, a refill, a modification, or a deletion. The pharmacy scans the card to retrieve order information, fills the order, and updates the pharmacy flag to indicate the prescription has been filled. The user scans the card on the user device to program the scheduled events, and the processing unit updates the user flag to indicate the operation has been taken, e.g., medication has been loaded or deleted. This "one card" will considerably simplify the life of the users and reduce potential errors that exist in the current process.

With the one card system, it is preferable that the system displays (or announces, for vision-impaired users) all medications currently in the system, and allows the user to select a medication and make desired request. The card may include other information, such as the next doctor appointment, which can also be programmed (as a scheduled event) to remind the user. Obviously, this one card system of the present invention is advantageous than the prior art electronic prescription, since it is used not only for filling the prescription, but also for programming the scheduled events and user-request expression.

In the preferred embodiment section, one exemplary user-request protocol is used where the number of scanning the programming information is used to identify a request. The programming-information reader may be configured to scan repeatedly with a predetermined interval and the system beeps (or produces other indication) for each successful scan. In that way, when the user hears the desired number of beeps, he/she takes away the programming-information carrier to indicate a selection. Or better yet, the system displays or announces applicable user requests, such as "taking" (medication), "loading", "deleting", and "reporting". When the desired user request is being displayed or announced, the user takes away the programming information to indicate a selection. Besides these exemplary user-request protocols, there are countless ways for user to express requests using the programming information. For example, the time duration of scanning the programming information may be used to identify the user requests, such as one second for taking a scheduled medication or requesting an emergency dose, two seconds for loading/refilling/modifying, three seconds for deleting, and four seconds for requesting a user-compliance report. Preferably, a signal corresponding to the preset time duration for each operation is produced, for example, one beep at the end of every second. Or alternatively, scanning programming information of a medication causes the system to display or announce all applicable requests sequentially (and repeatedly), and the user stops scanning (takes away the programming-information carrier) when the desired request is being displayed or announced.

In addition, multiple pieces of programming-information may be provided for each medication, each being used for a specific request. For example, one is encoded with a flag indicating loading (including refilling and modifying), one is encoded with a flag indicating scheduled or emergency dose, and one is encoded with a flag indicating deleting. Alternatively, one may use the programming information that contains a medication identifier to indicate a particular medication, and use separate pieces of programming information containing user request (one for loading/refilling/modifying, one for emergency dose, one for deleting, etc. for any medication) to indicate the user requests. Another alternative is that scanning the programming information of a user request causes the system to display or announce all existing medications, and the user stops scanning when the desired medication is being displayed or announced to indicate selection of the medication. For example, when user needs to delete a medication, he/she scans the programming information for deleting. This causes the system to display (or announce) all existing medication circularly. When the desired medication is being displayed (or announced), the user takes away the programming information. The processing unit understands that as request for deleting the selected medication, and proceeds accordingly. It should be emphasized that using these kinds of programming information that has user request does not amount to bypassing the user-request expression or eliminating the user-request protocol. Each of these methods of user request expression has certain rules that a user has to follow, which is precisely the user-request protocol.

For the user-interface that comprises a microphone and voice-recognition system, the user-request protocol may be using oral commands: "loading", "emergency", "deleting", etc. The oral commands are considered as programming information that contains the user requests, since it is machine-readable. Similarly, for the user-input interface that comprises a scanner and character-recognition system, users use printed usage information (e.g., two tablets at 8:00 AM, 12:00 PM, and 6:00 PM) and "loading", "emergency dose", "deleting" (in separate pieces) as programming information for user-request expression.

If the system is shared by multiple users (e.g., several members of a family, or in a healthcare facility), a user control means is needed. The user control means requires a user to present user identifier in predetermined form for certain types of user requests. Although a conventional user-identification interface such as a keypad or touch screen can be used for inputting user identifier, the preferred method is to use another piece of programming information that contains the user identifier, so that no additional user-input interface is not required. Pre-made distinct user identifier (e.g., barcode) may be provided (color coded or have the user's name printed or written on it). A user uses the programming information that contains the medication identifier to indicate a medication (if programming the scheduled events is required, encoded or preloaded usage information is required), and uses the programming information that contains the user identifier to express a request (e.g., single scan for taking scheduled or emergency dose, double scan for loading, triple scan for deleting, quadruple scan for user-compliance report). The processing unit registers the user identifier with medication when the medication is loaded. An alternative is, the user uses both the programming information that contains the usage information (or uses preloaded usage information) and that contains user identifier for loading medication, and uses that contains the user identifier for all other requests. When the user scans his/her user identifier, the system displays (or announces) all existing medications of the user circularly. The user takes away the user identifier when the desired medication is being displayed (or announced) to indicate selection of a medication. The system then displays (or announces) all applicable user requests for this medication circularly. The user scans his/her user identifier again when the desired user request is being displayed (or announced) to indicate selection of a user request. For devices used in healthcare facilities, the processing unit may be configured to allow only authorized person (identifier) to perform certain operations, just like system administrator for a computer system.

Another example for user control means is to use a fingerprint reader. The fingerprint of a designated finger (e.g., index finger of right hand) is used as user identifier. The fingerprint is considered as programming information, since it is machine-readable and identifies a user, although it requires a separate programming-information reader (the fingerprint reader). A user uses fingerprint just like a user identifier, as described above.

There are countless similar examples, they all follow the fundamental idea of the user-request expression of the present invention, namely, presenting (suitable) programming information to the programming-information reader in a predetermined manner indicates a specific user request.

In the preferred embodiment section (and the above description of this section), it is described that the user interface consists of a programming-information reader, and users use programming information (may be multiple pieces) to express all requests. The system can use other (conventional) controls, e.g., a control button (an on-and-off switch), for user-request expression in conjunction with the programming information. Again, there are countless possible user-request protocols for such configuration. One example may be: a user uses programming information that contains a medication identifier to indicate the medication, then, the user presses the control button once for taking a scheduled or emergency dose, twice for loading (including refilling and modifying), three times for deleting, four times for user-compliance report. A touch sensor switch or other equivalence can be used in place of the control button.

One variation is that the user holds down the control button for one second for taking a scheduled or emergency dose, two seconds for loading, three seconds for deleting, four seconds for user-compliance report.

Another variation is that the first time the programming information is scanned, the processing unit understands it as a loading request and proceeds accordingly. The subsequent scanning of the same programming information indicates other requests, and the user presses the control button once (or holds it for one second) for emergency dose, twice (or holds for two seconds) for loading, or three times (or holds for three seconds) for deleting, and four times (or holds for four seconds) for user-compliance report.

Yet another variation is that the user scans the programming information (once) for loading medication; for other requests that require identifying a medication, the user holds down the control button for a predetermined period of time (e.g., five seconds), which causes the system to display or announce all medications currently in the system; when the name of the desired medication is being displayed or announced, the user uses the control button to indicate the request: pressing the control button once for requesting an emergency dose, three times for deleting the medication, etc. For requests that do not require identifying a medication, the control button alone can be used to express requests, e.g., pressing the control button once for taking a scheduled dose, four times for user-compliance report.

Figure 11:
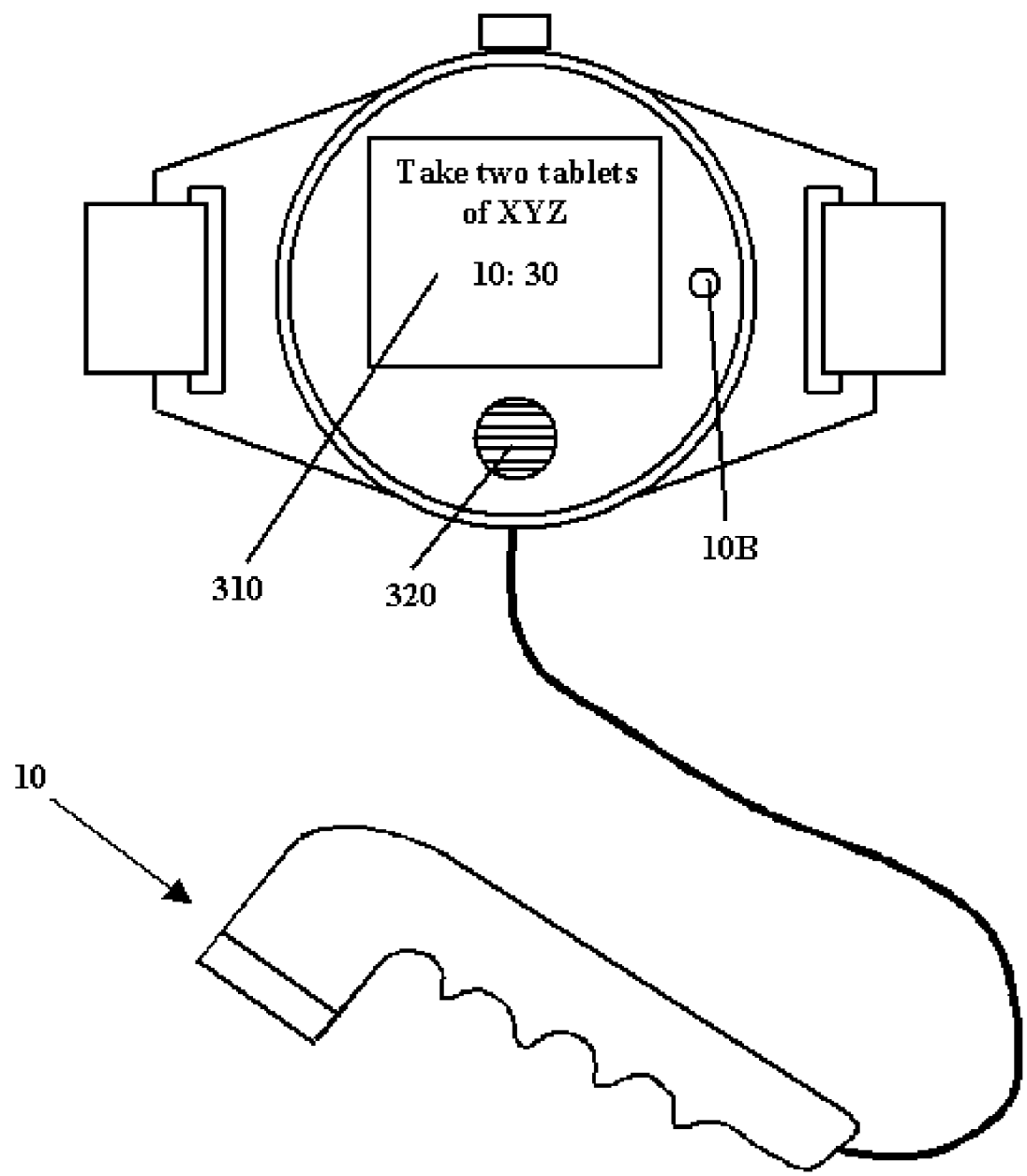
FIG. 11 shows yet another exemplary application of the present invention (with an optional control button): a medication reminder.

One exemplary embodiment with control button (as part of the user-input interface) is depicted in FIG. 11. The controlled device is an indicator, which has a LCD display 310 and an alarm 320. In this case, the system (control unit plus the controlled device) works as an auto-programming medication reminder. In this exemplary configuration, the processing unit and the controlled device (the indicator) are combined physically into a device that resembles a digital watch (upper portion of FIG. 11). FIG. 11 depicts that the programming-information reader 10 is plugged, ready to scan the programming information. The user scans the programming information, indicating request for loading. Although this particular embodiment (and some other similar situations) does not require loading the medication (medications may be stored in their original containers), for consistency the term loading is used. If necessary, the processing unit automatically programs the scheduled events using the programming information. The user unplugs the programming-information reader and wears the auto-programming medication reminder. Of course, wireless communication between the programming-information reader and processing unit can be used as well.

When a scheduled event occurs, the LCD display 310 shows the name and unit dosage of that medication, and the alarm 320 sounds. The user presses the control button 10B once to stop the alarm and takes the medication. The processing unit records the actual time when the programming information is scanned as user-compliance data. For all other requests (emergency dose, deletion, user-compliance report, etc.), the user holds down the control button 10B, which causes the display 310 to display all medications circularly. When the desired medication is being displayed, the user presses the control button 10B once for requesting an emergency dose, or three times for deleting the medication.

Another possible configuration is that the processing unit and the indicator (controlled device) are separate and communicate wirelessly, and a user wears the indicator. In this case, the programming-information reader and the processing unit may be integrated into a physical unit. Such configuration is suitable for short-range use, for example, inside and around a house or building. By the way, this exemplary embodiment does not require loading or deleting medication, hence guided user operation and automatic medication-storage mapping are not used.

Another replacement for control button is a mechanical-electrical lock. The lock may have multiple key positions, one for taking scheduled or emergency dose, one for loading, one for deleting, and one for user-compliance reporting. A user inserts his/her key to the lock and turns the desired position to make user request. Another variation is that inserting the key causes the system to display (announce) all current medications of the user. When the desired medication is being displayed, the user turns the key to indicate a selection. The system then displays (announces) all applicable user requests for the selected medication. When the desired user request is being displayed, the user turns or removes the key to indicate a selection. This embodiment not only provides an alternative method for user-request expression but also enforces security (the lock works as part of the user-input interface as well as the user control means).

Another example of conventional controls (as part of user-input interface) is a depressible scroll wheel (a scroll wheel plus a on-and-off switch). An exemplary user-request protocol may be: user uses programming information for loading medication. For all other requests, the user presses the scroll wheel once, which causes the display to show (or a speaker to announce) all medications in the system. The user uses the scroll wheel to scroll up or down the list to find the desired medication and presses the scroll wheel once, indicating a selection. Then, the display shows all applicable requests. The user uses the scroll wheel to find the desired request and presses the scroll wheel to indicate the selection. Since programming information alone is sufficient for user to express all requests, these additional controls are considered as optional controls.

In the preferred embodiment section, it is described that the system of the present invention has one programming-information reader. The system may also be equipped with multiple programming-information readers, each for a different type of programming-information carrier (e.g., barcode, magnetic strip, smart card, etc.). This gives medication providers more flexibility in choosing their preferred carriers, while giving users more flexibility in choosing their medication providers. These may be replaceable programming-information readers with a universal interface to the processing unit. This should not be confused with the redundant (identical) readers required by some prior art designs, which are simply due to the deficiency of the prior art designs.

Figure 12:
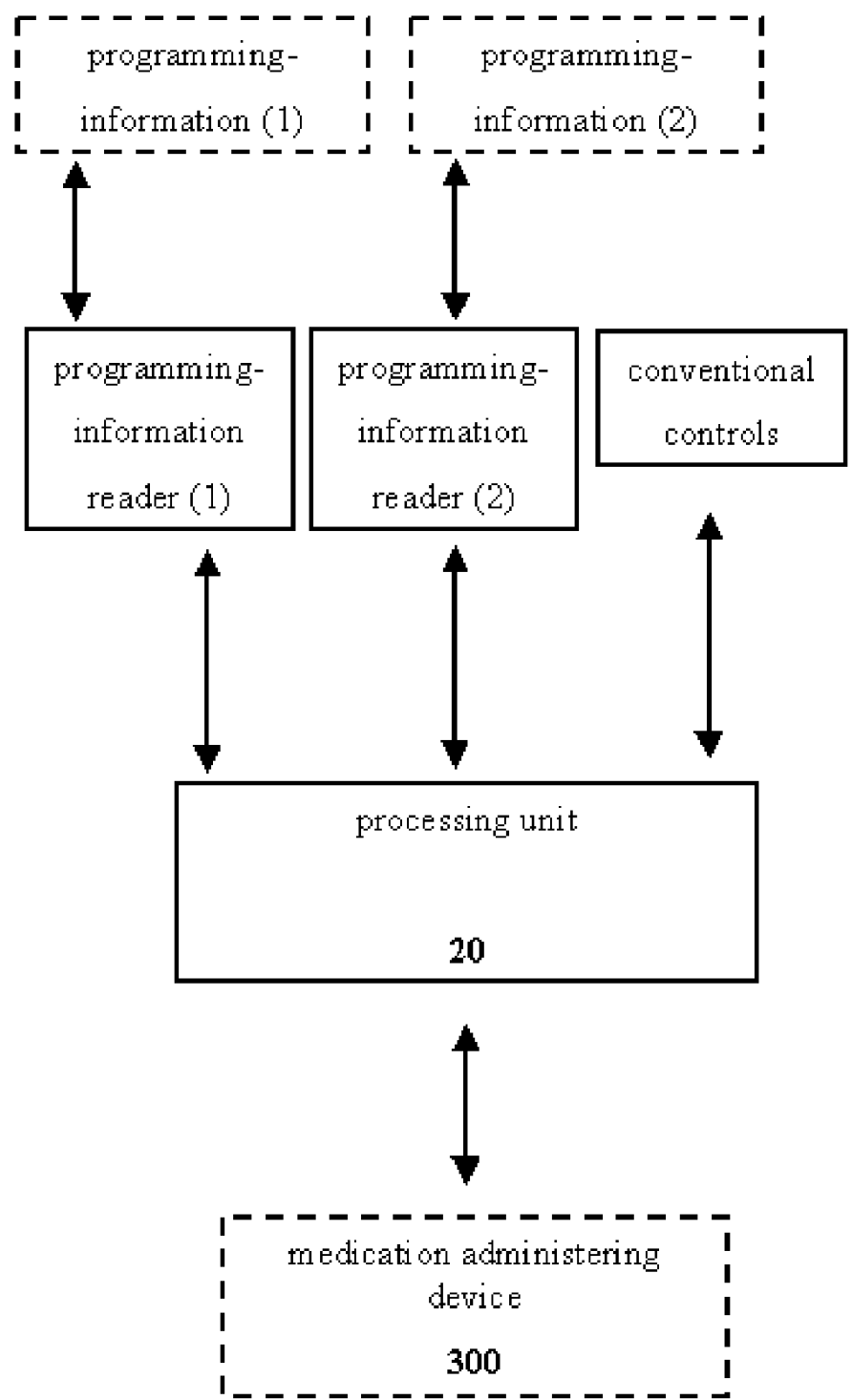
FIG. 12 shows the system of present invention with multiple (different types) programming-information reader and conventional controls.

FIG. 12 shows the system of the present invention with multiple (different types) programming-information readers and conventional controls. The programming-information readers can be barcode scanner, magnetic card reader, smart card reader, fingerprint reader, microphone, etc. The conventional controls can be control button, touch sensor, lock, scroll wheel, etc. The medication administering device (controlled device) can be medication reminder, organizer, dispenser, communication device, computer, etc.

There are countless embodiments for the user-input interface and corresponding user-request protocols, according to the fundamental idea of the present invention. A broad spectrum of such examples, from ordinary ones (using barcode, magnetic card, smart card, etc.) to extraordinary once (using human-voice, human-readable text, etc.), to combination with conventional controls (control button, lock, scroll wheel, etc.), has been described. The general rule is (1) programming information that contains medication identifier and usage information can be used for all types of user requests; (2) programming information medication that contains medication identifier (only) can be used for all types of user requests, except those require programming scheduled events (which need preloaded usage information); (3) other programming information or conventional controls can be used for some requests that do not require identifying a medication and programming scheduled events, otherwise they need help (e.g., programming information that contains medication identifier or usage information, or displayed list to chose a medication). The processing unit ignores invalid user requests (do not conform to the user-request protocol) and inapplicable (e.g., before a new medication is loaded, a user cannot request for deleting) user requests. And when it gives user choices, it only gives applicable ones to a given situation.

The system may have multiple sets of user-input interfaces and accept several user-request protocols. For example, the system may have the programming-information reader as the primary user-input interface and the control button as the backup user-input interface.

The new use of (machine-readable) programming information of the present invention allows the user to accomplish two tasks at the same time: conveying encoded information and user-request to the system. It allows simple user-request expression and simple user-input interface. Simple user-request expression and simple user-input interface should reduce the possibility of errors considerably. Nevertheless, the system may display or announce the user request as detected by the processing unit, and may be configured to require the user to confirm a request (using programming information or optional controls). Since any operation can be negated by the opposite operation, e.g., the effect of loading can be restored by a subsequent deleting and vise versa, users can always correct their mistakes gracefully.

In the preferred embodiment section, most examples describe that the processing unit generates control signals when a scheduled event occurs. The processing unit may as well generate control signals in advance to inform the user for future scheduled events. For example, the time, medication, and unit dosage of the next scheduled event may be displayed after the user takes a scheduled dose.

In the preferred embodiment section, it is described that the actual time that the programming information is scanned is used as user-compliance data. Other means can definitely be used to collect user-compliance data. For example, sensors (e.g., micro switches) that detect the opening/closing of compartment or access doors, or physical dispensing of medication, may be used.

In the preferred embodiment section, it is described that all necessary user operations are guided by the system. Obviously, the device manufacturer can decide to incorporate certain types of guided user operations at certain level to achieve desired effects. Depending on its capability, a particular system may require more, less, same, or different operations than those described in the preferred embodiment section, but suitable guidance can always be provided to guide the users to complete the necessary operations following the fundamental idea of the present invention.

In the preferred embodiment section, it is described that the user follows the guidance of the system to load a medication, and the processing unit establishes the medication-storage mapping. This is the preferred method since it solves two major problems for all prior art designs at same time. In some embodiments, loading is relatively easy, such as bulk organizer and dispenser, and the user can determine which compartment to load a medication to or delete from. In such case, an alternative way for automatic medication-storage mapping is to deploy sensors to detect which compartment a medication is loaded to or deleted from, similar to that in the description of the embodiment shown in FIG. 5A. Of course, it is also possible to use the programming information and/or the optional control (e.g., with a predetermined sequence) to establish the medication-storage mapping. For example, extend the user-request protocol to include the storage information (e.g., instead of requesting to load a medication, requesting to load a medication into a specific storage). Therefore, these two aspects of the present invention (guided user operation and automatic medication-storage mapping), are independent and can be used separately or combined.

In the preferred embodiment section, discrete scheduled events are mostly concerned. Generally speaking, the scheduled events do not have to be discrete events occurring at discrete moments, but can well be continuous events as a function of time. Examples may include controlling IV or anesthesia delivery with variable rate as function of time. Although in most cases a scheduled event contains two components: timing and quantity (e.g., unit dosage), in general it may contain any number and any type of components. For example, the scheduled event for take-as-needed medication contains only the quantity, and the scheduled event for reminding a user to measure blood pressure or glucose may be considered to contain only the timing or the timing plus a task (measurement).

In the preferred embodiment section, only the most basic form of the present invention is described. The system of the present invention certainly can incorporate additional components known in the art to add more features or detail. Since practically any complicated programming can be handled and is done automatically with the present invention, the correlation between the increase of features and the increase of user programming burden, which always exists with prior art designs, no longer exists. Furthermore, the present invention incorporates guided user operations. Therefore, the system of present invention is in advantageous position than prior art systems to incorporate more features.

For example, security measures may be added, such as secure caps/doors for medication storage, in order to prevent opening by children or unauthorized persons. For system used by multiple users, each user (identified by user identifier) can only access his/her own medication. The access doors may be latched and controlled by the processing unit, and the latches are released (or the medication is dispensed) only when the correct user identifier is presented (or a key is used).

In the preferred embodiment section, most examples describe a single controlled device. In principle, the method and control unit of the present invention can be used to control any number of identical or different devices simultaneously. For example, one control unit controls all medication administering devices of a household. Furthermore, the functions of several devices described in the preferred embodiment section may be combined (several devices combined), and the control unit controls all these functions. If the control unit controls multiple devices wirelessly, Bluetooth technology can be used.

The preferred embodiment section mainly describes the application of the present invention to user devices. The method and control unit of present invention can also be applied to control a pharmacy or factory (medication fulfillment) system. Such systems can be viewed as large-scale (slightly modified) bulk medication organizers/dispensers with hundreds or even thousands of storage compartments. The pharmacists use a programming information carrier (no schedule is needed) to load or delete a medication. The system provides guided operations to guide the pharmacists to load and delete the medication. However, there is no schedule involved. So, programming the scheduled events means register the necessary information (e.g., medication id, total amount, expiration date, etc.). The system automatically establishes medication-storage mapping. Another piece of programming information that contains the medication identifier and total quantity, which is generated by the doctor's computer when the medication is prescribed, may be used for filling a prescription. Preferably, the previously described one card is used. The pharmacists use the card to request the medication similar to requesting an emergency dose for user device, except that the "emergency dose" means the total amount of the prescribed medication. With features like automatic programming (medication and amount), simple user-request expressions, guided user operations, and automatic medication-storage mapping (storage registration), the pharmacy or factory system of the present invention is advantageous than those prior art pharmacy and factory systems. A large-scale system may call for a powerful processing unit or a stand-alone computer as the processing unit, but the fundamental idea and concept remain the same.

In the preferred embodiment section, for the sake of clarity, the system of the present invention is divided into two major components: programming-information reader and the processing unit. It is worth to emphasize again that these are logical divisions and not physical divisions. These logical components may be selectively combined, and some of their sub-components may be shared or moved from one component to another, as illustrated in the preferred embodiment section. Furthermore, these components should be understood and interpreted in the broadest context.

Finally, it must be emphasized that the exemplary embodiments are all designed to clearly convey the fundamental idea and spirit of the present invention. All the exemplary embodiments and components must be interpreted in the broadest sense, since it is impossible to describe exhaustively all possible choices. One example will be given here to illustrate such concept: programming information may be downloaded directly to the processing unit from the doctor's or pharmacy's computer system. It could be viewed that there was no programming-information carrier and programming-information reader. However, in the context consistent with the description of the present invention, it should be understood that in this case the programming-information carrier is the electric wires, light, or radio wave (depending on the transmission method used to download the programming information) that carries the signal of programming information, and the downloading port and the electric wires that fetch the signal of programming information to the processing unit constitute the programming-information reader. In such case the programming-information carrier only carries the programming information temporarily. But this is not totally different from the other examples in the preferred embodiment. As mentioned previously, re-writable programming-information carriers may be reused for different medications, so they also carry programming information (of a particular medication) temporarily.

A practical implementation of the example described immediately above is a smart card that contains the processing unit. The doctor's or pharmacy's computer system downloads the programming information into the smart card (wired or wirelessly). At user's home, the smart card controls the controlled devices (wired or wirelessly, e.g., using Bluetooth technology). The smart card detects all available controlled devices at user's home, chooses a suitable one for that medication, and guides the user to load the medication into appropriate magazine/compartment. The medication-storage mapping is automatically established with loading, and the smart card controls the scheduled events of the medication. In this case, it is preferable to have an indicator that can display (or announce) all medications in the system so that user can select a desired one to make applicable requests. For this exemplary embodiment, the system has two physical components: smart card (comprises the programming-information reader and processing unit) and controlled device. Even the two physical components can be further combined into one physical unit. A slight different configuration for this example is that the smart card implements only part of the processing unit, with the complementary part as a separate module or being integrated with the controlled device. However, this embodiment requires another programming-information reader or conventional control (with indicator) for user to express user requests.

The above example may sound in some aspect similar to some prior art designs, such as pharmacy-provided preprogrammed devices or doctor- or pharmacy-programmed module. It is considerably different from and is advantageous than those prior art designs, since it incorporates all the advantages of the present invention, such as flexibility in configuration, minimal user-input interface, simple user-request expressions, guided user operations, and automatic medication-storage mapping. It is auto-programmed as opposed to having to be programmed by pharmacist. Since it incorporates the guided user operation and automatic medication-storage mapping, the medication can be easily loaded by the user as opposed to having to be loaded (modified, deleted, etc.) by pharmacist as those prior art designs.

Conclusion, Ramification, and Scope

The present invention has five aspects. The first aspect of the present invention is automatic programming of the scheduled events. Hence user programming, user-programming interface, and user programming errors are all eliminated. The second aspect is simple user-request expression. Hence user input and the user-input interface are further reduced and simplified. The third aspect is guided user operation. The system guides the user to complete necessary operations corresponding to user request. Hence user operations are significantly simplified. The forth aspect is automatic medication-storage mapping. Hence the user no longer has to manually establish medication-storage mapping, and the user-input interface is further reduced. The fifth aspect is no clock setting. Hence clock-setting interface is eliminated and the user-input interface is further reduced. Prior art systems typically require the user to figure out a loading-scheduling plan, follow the plan to load the medications, and tell the system how the medications are stored and their scheduled events. The system of the present invention does the opposite: it figures out the loading-scheduling plan, guides the user to load the medications, establishes medication-storage mapping, and programs the scheduled events, all automatically.

The present invention can be used virtually with any type of medication administering devices (the preferred embodiment section describes all typical types), and can satisfy any needs. The more complicate the schedules, the more benefit the present invention provides.

The fundamental idea of the present invention can be apply to other areas that need to program and control any kind scheduled events, discrete or continuous. Examples may include dispensing parts/components in a factory assembly line, feeding ingredients/chemicals in food or chemical industry, control flow rate of a fluid (continuous function of time), controlling experiments in labs, or pet food/nutrition supplement dispensing. Incidentally, using (only) machine-readable programming information can prevent giving away business secret (e.g., recipe, composition, timing, and condition). The simple user-request expressions, guided user operations, and automatic medication-storage mapping will further improve the operation of these systems. Obviously, when the present invention is applied to more complex controls, every aspect (e.g., the scheduled events, types of operations) becomes more complex than that for controlling medication administering device, but the fundamental concept and the method remain the same. All such applications are within the scope of the present invention. For the general application of the present invention, the term "object" should be used in place of "medication" (e.g., object identifier, object-storage mapping, etc.), and most descriptions should apply to the general applications. For general applications, the scheduled event may contain timing, quantity, number, length, area, volume, temperature, pressure, flow rate, speed, acceleration, force, torque, voltage, current, field strength, frequency, or any task. Also, the user requests for different objects are different, and the operation corresponding to the requests are also different, but they all follow the same pattern as described.

In conclusion, the system of the present invention provides the following advantages over the prior art designs:

(1) It satisfies all practical needs for medication management and administration (overcomes prior art disadvantages A1 and G5).
(2) It automatically programs the schedules and unit dosages of medications, hence eliminating user programming, user-programming interface, and user-programming error (overcomes prior art disadvantages B1, C2, D3, E2, and E3).
(3) It automatically tracks the scheduled events and takes appropriate actions when a scheduled event occurs (overcomes prior art disadvantages A2, A3, B7, and B8).
(4) It allows users to express requests with very simple manner and has a minimal user-input interface (overcomes prior art disadvantage J1).
(5) It guides the user to complete all necessary user operations (overcomes prior art disadvantages B2, B3, B5, B6, D1, E4, J2).
(6) It automatically establishes medication-storage mapping without any additional user effort (overcomes prior art disadvantages E5 and J3).
(7) It does not require clock setting and clock-setting interface (overcomes prior art disadvantages C1, E1, and I12).
(8) It has a minimal user-input interface, requires minimum and simple user operations, and reduces the user-operation errors associated with prior art designs (overcomes a common disadvantage of all prior art designs).
(9) It can be used by any number of users, can control any number of devices, can handle any number of medications, with any precise timings, any different schedules, and any complex schedules (overcomes prior art disadvantages B4, D2, I4).
(10) Vision-impaired users and other users that are excluded by prior art systems and devices can easily use (solves a long-standing problem for all prior art devices).
(11) It is so easy to use hence there is no longer a need for professional assistance or have medications prepackaged (overcomes prior art disadvantages F2 to F13, G1, G2, I7, and H6).
(12) Users are not required to subscribe to any organization for managing their medications and no large supporting system is needed (overcomes prior art disadvantages H1 to H7).
(13) It does not require redundant components (overcomes prior art disadvantages I5, I6, and I8).
(14) It can be adopted for all types of medication administering devices (overcomes prior art disadvantage I9).
(15) It basically has no restrictions on configuration, dimension, interconnection among its components, and detailed design of the controlled device, hence gives the device manufacturers maximum freedom in design their devices (overcomes prior art disadvantages I2, I3, I10 and I11).
(16) It does not require medication providers to drastically change their routines, equipments, or medication packages (overcomes prior art disadvantages G3 and I1).
(17) Users can freely choose their medication providers and medication administering devices (overcomes prior art disadvantage F1).
(18) It is of low cost (no subscription and maintenance fee) to users (overcomes prior art disadvantages G4).

The five aspects of the present invention, namely, automatic programming of scheduled events, simple user-request expression, guided user operation, automatic medication-storage mapping, and no clock setting, can be selectively combined (some of them can be applied separately) to achieve certain effects or satisfy certain requirements. Each of them overcomes a number of the aforementioned prior art disadvantage. Each of them reduces or simplifies the physical complexity, the components, and the user operations. Each of them reduces potential errors associated with the prior art designs. Combining all these aspects together, the present invention overcomes all aforementioned disadvantages of the prior art designs, significantly simplifies or reduces the complexity, the components, the operations, and the potential operation errors of the prior art designs, and greatly simplifies the user operations, resulting a truly accurate, highly automatic and user-friendly system. Due to its high level of automation and ease of use, vision-impaired users and other users that are excluded by prior art systems can easily use the system of the present invention.

Furthermore, the present invention basically has no restriction on configurations, dimensions, or detailed designs of the components of the system. The components can be separate or selectively integrated. The components can communicate through any suitable wired or wireless communication links. Some sub-components can be shared or moved around. No prior art method or system has such broad range of application and such flexibility. No prior art designs or combination of them provides so many advantages. No prior art design provides such level of automation, has such simple user-input interface, and is so easy to use.

The method and control unit of the present invention can make a significant impact if it is widely adopted and standard protocols are established. Device manufacturers can design their devices whatever way they want. They can even choose to make modules of part of the system to work with the complementary modules made by others, and the only requirement is that they all follow the standard protocols. Medication providers can choose whatever package and container they want. Programming information can come from doctors, medication providers, or pre-made templates or pre-loaded ones can be used. Users can get their medication from any medication provider, and choose any device they like.

Given the exemplary embodiments, numerous alternations, substitutions, modifications, and ramifications will become obvious to the skilled in the art. The present embodiments therefore should be considered in all respects as illustrative and not restrictive. All alternations, substitutions, modifications, and ramifications that come within the meaning and range of equivalency of the present invention are covered by the scope of the present invention. The scope of the present invention should be determined not by the exemplary embodiments just described, but by the following claims.

What is claimed is:

1. A method for programming and controlling scheduled events for at least one object, comprising the steps of
    (a) providing a programming-information carrier encoded with predetermined programming information concerning said object,
    (b) providing a programming-information reader that is capable of reading said programming information from said programming-information carrier and converting it into appropriate programming-information signals,
    (c) providing a predetermined user-request protocol that includes a plurality of predetermined user requests, where presenting said programming-information carrier to said programming-information reader in a predetermined manner indicates a specific user request,
(d) providing a processing unit that couples to said programming-information reader, said processing unit comprising a processor, a clock and a memory unit, and being programmed to
  (1) decode said programming information from said programming-information signals,
  (2) determine said user requests according to said user-request protocol,
  (3) selectively use said programming information to take predetermined control actions in response to said user requests, said control actions including programming said scheduled events and generating control signals accordingly,
whereby a user can express different requests dynamically using said programming-information carrier, said scheduled events are programmed and controlled automatically without user manual input.

2. The method of claim 1 wherein said programming information contains object identifier of at least one said object and said processing unit can further access preloaded information with said object identifier and selectively use said preloaded information for certain types of said control actions.

3. The method of claim 1 wherein said processing unit further couples to suitable guiding means, and said control actions further include generating guiding signals to drive said guiding means to guide the user to complete predetermined user operations corresponding to certain types of said user requests.

4. The medication administering device of claim 1 wherein said programming-information carrier is of the type selected from the group consisting of barcode, magnetic card, radio-frequency tag, smart card, diskette, portable hard drive, flash memory, compact disk, magnetic tape, optical memory device, biological memory device, and printed text.

5. The method of claim 1 wherein said object is a substance stored in at least one storage, said scheduled event concerns releasing certain amount of said substance from certain storage, and said control actions include automatic medication-storage mapping based on a method selected from the group consisting of guided user operation and sensed user operation.

6. A control unit for controlling at least one medication administering unit, comprising:
(a) at least one programming-information reader that is capable of reading encoded programming information concerning at least one medication from at least one type of programming-information carrier and convening it into appropriate programming-information signals,
(b) a processing unit that couples to said programming-information reader, said processing unit comprising a processor, a clock, and a memory unit, and being programmed to
  (1) decode said programming information from said programming-information signals,
  (2) selectively use said programming information to take predetermined control actions, said control actions including programming at least one scheduled medication administering event, providing guidance to guide the user to complete predetermined user operations, and generating predetermined control signals accordingly to control said medication administering unit,
  (3) determine user requests according to a predetermined user-request protocol and take predetermined actions accordingly, said user-request protocol including a plurality of predetermined user requests, where presenting said programming-information carrier to said programming-information reader in a predetermined manner indicates a specific user request.

7. A medication administering device, comprising:
(a) at least one programming-information reader that is capable of reading encoded programming information concerning at least one medication from at least one type of programming-information carrier and converting it into appropriate programming-information signals,
(b) a medication administering unit that comprises a plurality of storages for different types of medications,
(c) a processing unit that couples to said programming-information reader and said medication administering unit, said processing unit comprising a processor, a clock, and a memory unit, and being programmed to
  (1) decode said programming information from said programming-information signals,
  (2) selectively use said programming information to take predetermined control actions, said control actions including programming at least one scheduled medication administering event for at least one medication, establishing medication-storage mapping for said medication, and generating predetermined control signals accordingly to control said medication administering unit,
  (3) determine user requests according to a predetermined user-request protocol and take predetermined actions accordingly, said user-request protocol including a plurality of predetermined user requests, where presenting said programming-information carrier to said programming-information reader in a predetermined manner indicates a specific user request,
(d) said medication administering unit taking predetermined controlled actions in response to said control signals, said controlled actions including at least one selected from the group consisting of producing alarm, indicating a medication, indicating unit dosage, indicating time, indicating storage, indicating said scheduled administering event, indicating scheduled future administering event, and dispensing a medication.

* * * * *